(12) United States Patent
Krüger et al.

(10) Patent No.: US 6,747,046 B2
(45) Date of Patent: Jun. 8, 2004

(54) SUBSTITUTED N-(1,4,5,6-TETRAHYDRO-CYCLOPENTAPYRAZOL-3-YL) DERIVATIVES, THEIR PRODUCTION AND USE AS PHARMACEUTICAL AGENTS

(75) Inventors: Martin Krüger, Berlin (DE); Olaf Prien, Berlin (DE); Andreas Steinmeyer, Berlin (DE); Jörg Kroll, Berlin (DE); Alexander Ernst, Berlin (DE); Gerhard Siemeister, Berlin (DE); Martin Haberey, Berlin (DE); Jens Hoffmann, Mühlenbeck (DE)

(73) Assignee: Schering Aktiengesellschaft, Berlin (DE)

( * ) Notice: Subject to any disclaimer, the term of this patent is extended or adjusted under 35 U.S.C. 154(b) by 0 days.

(21) Appl. No.: 10/253,910

(22) Filed: Sep. 25, 2002

(65) Prior Publication Data

US 2003/0212121 A1 Nov. 13, 2003

(30) Foreign Application Priority Data

Sep. 25, 2001 (DE) .......................................... 101 48 618

(51) Int. Cl.[7] .................... C07D 231/54; A61K 31/416; A61P 35/00
(52) U.S. Cl. ....................... 514/338; 514/378; 514/407; 546/275.7; 548/236; 548/360.1
(58) Field of Search ................................ 514/407, 338, 514/378; 546/275.7; 548/236, 360.1

(56) References Cited

U.S. PATENT DOCUMENTS

| 6,218,418 B1 | 4/2001 | Pevarello et al. |
| 6,291,504 B1 | 9/2001 | Nugiel et al. |

Primary Examiner—Joseph K. McKane
Assistant Examiner—Andrea D Small
(74) Attorney, Agent, or Firm—Millen, White, Zelano & Branigan, P.C.

(57) ABSTRACT

Substituted N-(1,4,5,6-tetrahydro-cyclopentapyrazol-3-yl) derivatives, their production, as well as intermediate products for their production, and the use as pharmaceutical agents for treating various diseases are described.

9 Claims, 1 Drawing Sheet

SUBSTITUTED N-(1,4,5,6-TETRAHYDRO-CYCLOPENTAPYRAZOL-3-YL) DERIVATIVES, THEIR PRODUCTION AND USE AS PHARMACEUTICAL AGENTS

The invention relates to substituted N-(1,4,5,6-tetrahydro-cyclopentapyrazol-3-yl) derivatives, their production and use as pharmaceutical agents for treating various diseases.

Known from DE 198 54 081 A1 or WO 00/31066 are substituted N-pyrazolyl-phenoxynicotinic acid-(thio)amides that are used as herbicides. These compounds clearly differ structurally from the compounds according to the invention, however.

From WO 01/12189, 3(5)-amino-pyrazole derivatives and their use as pharmaceutical agents, especially for treating cancer and cell-proliferative diseases, are known. These compounds also differ from the compounds according to the invention by their structure, especially on the pyrazole ring.

There is still a great need for effective pharmaceutical agents for treating cancer and other cell-proliferative diseases.

It has now been found that compounds of general formula I

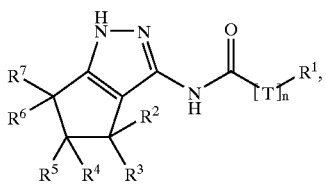

(I)

in which

R$^1$ stands for linear or branched C$_1$–C$_6$-alkyl, C$_2$–C$_6$-alkenyl, C$_2$–C$_6$-alkinyl, C$_1$–C$_6$-alkoxy, C$_1$–C$_6$-alkylthio or C$_3$–C$_{12}$-cycloalkyl, C$_3$–C$_{12}$-cycloalkenyl, C$_3$–C$_{12}$-heterocycloalkyl, C$_3$–C$_{12}$-heterocycloalkenyl, aryl or heteroaryl, which optionally can be substituted in one or more places in the same way or differently, R$^2$ and R$^3$ are the same or different and stand for hydrogen, linear or branched C$_1$–C$_6$-alkyl, C$_2$–C$_6$-alkenyl, C$_2$–C$_6$-alkinyl or C$_1$–C$_6$-alkoxy, which optionally can be substituted in one or more places in the same way or differently, R$^4$ and R$^5$ are the same or different and stand for hydrogen, halogen, linear or branched C$_1$–C$_6$-alkyl, C$_2$–C$_6$-alkenyl, C$_2$–C$_6$-alkinyl or C$_1$–C$_6$-alkoxy, which optionally can be substituted in one or more places in the same way or differently, or together stand for a carbonyl group, or together form a cyclic five- or six-ring-acetal with O,O; N,O; O,S; or S,S, which optionally can be substituted with C$_1$–C$_6$-alkyl, or R$^2$ and R$^4$ together form a C$_3$–C$_{12}$-cycloalkyl ring or a C$_3$–C$_{12}$-cycloalkenyl ring, which optionally can be substituted in one or more places in the same way or differently, R$^6$ and R$^7$ are the same or different and stand for hydrogen, linear or branched C$_1$–C$_6$-alkyl, C$_2$–C$_6$-alkenyl or C$_2$–C$_6$-alkinyl, which optionally can be substituted in one or more places in the same way or differently, or together form a C$_3$–C$_{12}$-cycloalkyl ring or a C$_3$–C$_{12}$-cycloalkenyl ring, which optionally can be substituted in one or more places in the same way or differently, or R$^5$ and R$^6$ optionally together form a double bond, or R$^5$ and R$^6$ together form a C$_3$–C$_{12}$-cycloalkyl ring or a C$_3$–C$_{12}$-cycloalkenyl ring, which optionally can be substituted in one or more places in the same way or differently, T stands for —CH$_2$—, —O—, —CH$_2$=CH$_2$—, —CH≡CH—, —CH$_2$—O—CH$_2$—, —CH$_2$—O—, —O—CH$_2$— or =CO, and n stands for 0–6, as well as tautomers, isomers and salts thereof.

Alkyl is defined in each case as a straight-chain or branched alkyl radical, such as, for example, methyl, ethyl, propyl, isopropyl, butyl, isobutyl, sec-butyl, tert-butyl, pentyl, isopentyl or hexyl.

Alkoxy is defined in each case as a straight-chain or branched alkoxy radical, such as, for example, methyloxy, ethyloxy, propyloxy, isopropyloxy, butyloxy, isobutyloxy, sec-butyloxy, tert-butyloxy, pentyloxy, isopentyloxy or hexyloxy.

Alkythio is defined in each case as a straight-chain or branched alkylthio radical, such as, for example, methylthio, ethylthio, propylthio, isopropylthio, butylthio, isobutylthio, sec-butylthio, tert-butylthio, pentylthio, isopentylthio or hexylthio.

Cycloalkyls are defined as monocyclic alkyl rings, such as cyclopropyl, cyclobutyl, cyclopentyl, cyclohexyl, or cycloheptyl, cyclooctyl, cyclononyl or cyclodecyl, but also bicyclic rings or tricyclic rings, such as, for example, norbornyl, adamantanyl, etc.

Cycloalkenyl is defined in each case as cyclobutenyl, cyclopentenyl, cyclohexenyl, cycloheptenyl, cyclooctenyl, cyclononenyl or cyclodecenyl, whereby the linkage can be carried out both to the double bond and to the single bonds.

Halogen is defined in each case as fluorine, chlorine, bromine or iodine.

Alkenyl is defined in each case as a straight-chain or branched alkenyl radical that contains 2–6, preferably 2–4, C atoms. For example, the following radicals can be mentioned: vinyl, propen-1-yl, propen-2-yl, but-1-en-1-yl, but-1-en-2-yl, but-2-en-1-yl, but-2-en-2-yl, 2-methyl-prop-2-en-1-yl, 2-methyl-prop-1-en-1-yl, but-1-en-3-yl, but-3-en-1-yl, and allyl.

Alkinyl is defined in each case as a straight-chain or branched alkinyl radical that contains 2–6, preferably 2–4, C atoms. For example, the following radicals can be mentioned: acetylene, propin-1-yl, propin-3-yl, but-1-in-1-yl, but-1-in-4-yl, but-2-in-1-yl, but-1-in-3-yl, etc.

The aryl radical in each case comprises 3–12 carbon atoms, and can be benzocondensed in each case.

For example, there can be mentioned: cyclopropenyl, cyclopentadienyl, phenyl, tropyl, cyclooctadienyl, indenyl, naphthyl, azulenyl, biphenyl, fluorenyl, anthracenyl, etc.

The heteroaryl radical in each case comprises 3–16 ring atoms, and instead of carbon, the radical can contain one or more heteroatoms that are the same or different, such as oxygen, nitrogen or sulfur in the ring, and can be monocyclic, bicyclic or tricyclic, and in addition in each case can be benzocondensed.

For example, there can be mentioned:

Thienyl, furanyl, pyrrolyl, oxazolyl, thiazolyl, imidazolyl, pyrazolyl, isoxazolyl, isothiazolyl, oxadiazolyl, triazolyl, thiadiazolyl, etc. and benzo derivatives thereof, such as, e.g., benzofuranyl, benzothienyl, benzoxazolyl, benzimidazolyl, indazolyl, indolyl, isoindolyl, etc.; or pyridyl, pyridazinyl, pyrimidinyl, pyrazinyl, triazinyl, etc. and benzo derivatives thereof, such as, e.g., quinolyl, isoquinolyl, etc.; or oxepinyl, azocinyl, indolizinyl, indolyl, isoindolyl, indazolyl, benzimidazolyl, purinyl, etc. and benzo derivatives thereof; or quinolinyl, isoquinolinyl, cinnolinyl, phthalazinyl, quinazolinyl, quinoxalinyl, naphthyridinyl, pteridinyl, carbazolyl, acridinyl, phenazinyl, phenothiazinyl, phenoxazinyl, xanthenyl, etc.

Heterocycloalkyl stands for an alkyl ring that comprises 3–12 carbon atoms and that instead of carbon contains one or more heteroatoms that are the same or different, such as, e.g., oxygen, sulfur or nitrogen.

As heterocycloalkyls, there can be mentioned, e.g.: oxiranyl, oxethanyl, aziridinyl, azetidinyl, tetrahydrofuranyl, pyrrolidinyl, dioxolanyl, imidazolidinyl, pyrazolidinyl, dioxanyl, piperidinyl, morpholinyl, dithianyl, thiomorpholinyl, piperazinyl, trithianyl, quinuclidinyl, etc.

Heterocycloalkenyl stands for an alkyl ring that comprises 3–12 carbon atoms and that instead of carbon contains one or more heteroatoms that are the same or different, such as, e.g., oxygen, sulfur or nitrogen, and that is partially saturated.

As heterocycloalkenyls, there can be mentioned, e.g.: pyran, thiine, dihydroazete, etc.

Cyclic acetal stands for a ring, such as, e.g.,

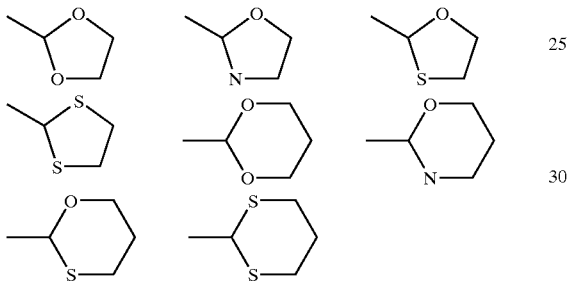

which optionally can be substituted with a $C_1$–$C_6$-alkyl group.

The aryl radical and the heteroaryl radical can be substituted in each case in one or more places in the same way or differently with hydroxy, halogen, amino, $C_{1-6}$-alkyl, $C_{1-6}$-alkoxy, $C_{1-6}$-alkylthio, halo-$C_{1-6}$-alkyl, halo-$C_{1-6}$-alkoxy, $C_{1-6}$-alkoxycarbonyl, cyano, nitro, $C_{1-6}$-alkylsulfanyl, $C_{1-6}$-alkylsulfinyl, $C_{1-6}$-alkylsulfonyl, or with the group —C(O)$C_{1-6}$-alkyl, —NH$C_{1-6}$-alkyl, —N-di-$C_{1-6}$-alkyl, —CONH$_2$, —CONH$C_{1-6}$-alkyl or —CON-di-$C_{1-6}$-alkyl, or can be substituted with another aryl or heteroaryl radical, which optionally itself can be substituted in one or more places in the same way or differently with hydroxy, halogen, amino, $C_{1-6}$-alkyl, $C_{1-6}$-alkoxy, $C_{1-6}$-alkylthio, halo-$C_{1-6}$-alkyl, halo-$C_{1-6}$-alkoxy, $C_{1-6}$-alkoxycarbonyl, cyano, nitro, $C_{1-6}$-alkylcarbonyl, $C_{1-6}$-alkylsulfanyl, $C_{1-6}$-alkylsulfinyl, $C_{1-6}$-alkylsulfonyl, or with the group —C(O)$C_{1-6}$-alkyl, —NH$C_{1-6}$-alkyl, —N-di-$C_{1-6}$-alkyl, —CONH$_2$, —CONH$C_{1-6}$-alkyl or —CON-di-$C_{1-6}$-alkyl.

If an acid group is included, the physiologically compatible salts of organic and inorganic bases are suitable as salts, such as, for example, the readily soluble alkali salts and alkaline-earth salts as well as N-methyl-glucamine, dimethyl-glucamine, ethyl-glucamine, lysine, 1,6-hexadiamine, ethanolamine, glucosamine, sarcosine, serinol, tris-hydroxy-methyl-amino-methane, aminopropanediol, Sovak base, and 1-amino-2,3,4-butanetriol.

If a basic group is included, the physiologically compatible salts of organic and inorganic acids are suitable, such as hydrochloric acid, sulfuric acid, phosphoric acid, citric acid, tartaric acid, fumaric acid, i.a.

Those compounds of general formula I, in which $R^1$ stands for linear or branched $C_1$–$C_6$-alkyl, $C_2$–$C_6$-alkenyl, $C_2$–$C_6$-alkinyl, $C_1$–$C_6$-alkoxy, $C_1$–$C_6$-alkylthio or $C_3$–$C_{12}$-cycloalkyl, $C_3$–$C_{12}$-cycloalkenyl, $C_3$–$C_{12}$-heterocycloalkyl, $C_3$–$C_{12}$-heterocycloalkenyl, aryl or heteroaryl, which optionally can be substituted in one or more places in the same way or differently with hydroxy, halogen, amino, $C_{1-6}$-alkyl, $C_{1-6}$-alkoxy, $C_{1-6}$-alkylthio, halo-$C_{1-6}$-alkyl, halo-$C_{1-6}$-alkoxy, $C_{1-6}$-alkoxycarbonyl, cyano, nitro, $C_{1-6}$-alkylsulfinyl, $C_{1-6}$-alkylsulfinyl, $C_{1-6}$-alkylsulfonyl, or with the group —C(O)$C_{1-6}$-alkyl, —NH$C_{1-6}$-alkyl, —N-di-$C_{1-6}$-alkyl, —CONH$_2$, —CONH$C_{1-6}$-alkyl or —CON-di-$C_{1-6}$-alkyl, or can be substituted with another aryl radical or heteroaryl radical that optionally itself can be substituted in one or more places in the same way or differently, $R^2$ and $R^3$ are the same or different and stand for hydrogen, linear or branched $C_1$–$C_6$-alkyl, $C_2$–$C_6$-alkenyl, $C_2$–$C_6$-alkinyl or $C_1$–$C_6$-alkoxy, which optionally can be substituted in one or more places in the same way or differently with hydroxy, halogen, amino, $C_{1-6}$-alkoxy, or with the group —NH$C_{1-6}$-alkyl or —N-di-$C_{1-6}$-alkyl, $R^4$ and $R^5$ are the same or different and stand for hydrogen, halogen, linear or branched $C_1$–$C_6$-alkyl, $C_2$–$C_6$-alkenyl, $C_2$–$C_6$-alkinyl or $C_1$–$C_6$-alkoxy, which optionally can be substituted in one or more places in the same way or differently with hydroxy, halogen, amino, $C_{1-6}$-alkoxy, or with the group —NH$C_{1-6}$-alkyl or —N-di-$C_{1-6}$-alkyl, or together stand for a carbonyl group, or together form a cyclic five- or six-ring-acetal of the structure

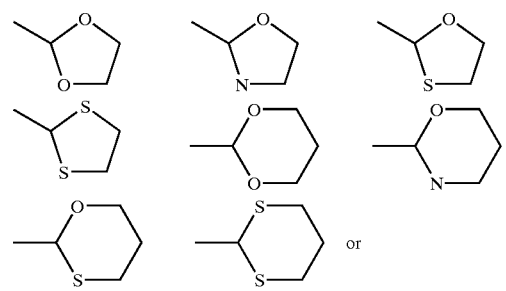

or $R^2$ and $R^4$ together form a $C_3$–$C_{12}$-cycloalkyl ring or a $C_3$–$C_{12}$-cycloalkenyl ring, which optionally can be substituted in one or more places in the same way or differently with hydroxy, halogen, amino, $C_{1-6}$-alkoxy, or with the group —NH$C_{1-6}$-alkyl or —N-di-$C_{1-6}$-alkyl, or $R^3$ and $R^5$ together form a $C_3$–$C_{12}$-cycloalkyl ring or a $C_3$–$C_{12}$-cycloalkenyl ring, which optionally can be substituted in one or more places in the same way or differently with hydroxy, halogen, amino, $C_{1-6}$-alkoxy, or with the group —NH$C_{1-6}$-alkyl or —N-di-$C_{1-6}$-alkyl, $R^6$ and $R^7$ are the same or different and stand for hydrogen, linear or branched $C_1$–$C_6$-alkyl, $C_2$–$C_6$-alkenyl or $C_2$–$C_6$-alkinyl, which optionally can be substituted in one or more places in the same way or differently with hydroxy, halogen, amino, $C_{1-6}$-alkoxy, or with the group —NH$C_{1-6}$-alkyl or —N-di-$C_{1-6}$-alkyl, or together form a $C_3$–$C_{12}$-cycloalkyl ring or a $C_3$–$C_{12}$-cycloalkenyl ring, which optionally can be substituted in one or more places in the same way or differently with hydroxy, halogen, amino, $C_{1-6}$-alkoxy, or with the group —$NHC_{1-6}$-alkyl or —N-di-$C_{1-6}$-alkyl, or $R^5$ and $R^6$ optionally together form a double bond, T stands for —$CH_2$—, —O—, —$CH_2$=$CH_2$—, —CH≡CH—, —$CH_2$—O—$CH_2$—, —$CH_2$—O—, —O—$CH_2$— or =CO, and n stands for 0–6, as well as tautomers, isomers and salts thereof, have proven especially valuable.

Those compounds of general formula I, in which $R^1$ stands for linear or branched $C_1$–$C_6$-alkyl, $C_2$–$C_6$-alkenyl, $C_2$–$C_6$-alkinyl, $C_1$–$C_6$-alkoxy, $C_1$–$C_6$-alkylthio or $C_3$–$C_{12}$-cycloalkyl, $C_3$–$C_{12}$-cycloalkenyl, $C_3$–$C_{12}$-heterocycloalkyl, $C_3$–$C_{12}$-heterocycloalkenyl, aryl or heteroaryl, which optionally can be substituted in one or more places in the same way or differently with hydroxy, halogen, amino, $C_{1-6}$-alkyl, $C_{1-6}$-alkoxy, $C_{1-6}$-alkylthio, halo-$C_{1-6}$-alkyl, halo-$C_{1-6}$-alkoxy, $C_{1-6}$-alkoxycarbonyl, cyano, nitro, $C_{1-6}$-alkylsulfanyl, $C_{1-6}$-alkylsulfinyl, $C_{1-6}$-alkylsulfonyl, or with the group —C(O)$C_{1-6}$-alkyl, —$NHC_{1-6}$-alkyl, —N-di-$C_{1-6}$-alkyl, —$CONH_2$, —$CONHC_{1-6}$-alkyl or —CON-di-$C_{1-6}$-alkyl, or can be substituted with another aryl or heteroaryl radical, which optionally itself can be substituted in one or more places in the same way or differently with hydroxy, halogen, amino, $C_{1-6}$-alkyl, $C_{1-6}$-alkoxy, $C_{1-6}$-alkylthio, halo-$C_{1-6}$-alkyl, halo-$C_{1-6}$-alkoxy, $C_{1-6}$-alkoxycarbonyl, cyano, nitro, $C_{1-6}$-alkylcarbonyl, $C_{1-6}$-alkylsulfanyl, $C_{1-6}$-alkylsulfinyl, $C_{1-6}$-alkylsulfonyl, or with the group —C(O)$C_{1-6}$-alkyl, —$NHC_{1-6}$-alkyl, —N-di-$C_{1-6}$-alkyl, —$CONH_2$, —$CONHC_{1-6}$-alkyl or —CON-di-$C_{1-6}$-alkyl, $R^2$ and $R^3$ are the same or different and stand for hydrogen, linear or branched $C_1$–$C_6$-alkyl, $C_2$–$C_6$-alkenyl, $C_2$–$C_6$-alkinyl or $C_1$–$C_6$-alkoxy, which optionally can be substituted in one or more places in the same way or differently with hydroxy, halogen, amino, $C_{1-6}$-alkoxy, or with the group —$NHC_{1-6}$-alkyl or —N-di-$C_{1-6}$-alkyl, $R^4$ and $R^5$ are the same or different and stand for hydrogen, halogen, linear or branched $C_1$–$C_6$-alkyl, $C_2$–$C_6$-alkenyl, $C_2$–$C_6$-alkinyl or $C_1$–$C_6$-alkoxy, which optionally can be substituted in one or more places in the same way or differently with hydroxy, halogen, amino, $C_{1-6}$-alkoxy, or with the group —$NHC_{1-6}$-alkyl or —N-di-$C_{1-6}$-alkyl, or together stand for a carbonyl group, or together form a cyclic five- or six-ring-acetal of the structure

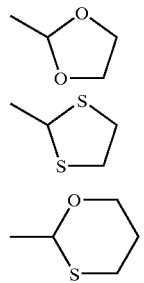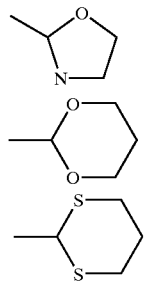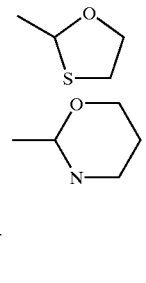

or $R^2$ and $R^4$ together form a $C_3$–$C_{12}$-cycloalkyl ring or a $C_3$–$C_{12}$-cycloalkenyl ring, which optionally can be substituted in one or more places in the same way or differently with hydroxy, halogen, amino, $C_{1-6}$-alkoxy, or with the group —$NHC_{1-6}$-alkyl or —N-di-$C_{1-6}$-alkyl, or $R^3$ and $R^5$ together form a $C_3$–$C_{12}$-cycloalkyl ring or a $C_3$–$C_{12}$-cycloalkenyl ring, which optionally can be substituted in one or more places in the same way or differently with hydroxy, halogen, amino, $C_{1-6}$-alkoxy, or with the group —$NHC_{1-6}$-alkyl or —N-di-$C_{1-6}$-alkyl, $R^6$ and $R^7$ are the same or different and stand for hydrogen, linear or branched $C_1$–$C_6$-alkyl, $C_2$–$C_6$-alkenyl or $C_2$–$C_6$-alkinyl, which optionally can be substituted in one or more places in the same way or differently with hydroxy, halogen, amino, $C_{1-6}$-alkoxy, or with the group —$NHC_{1-6}$-alkyl or —N-di-$C_{1-6}$-alkyl, or together form a $C_3$–$C_{12}$-cycloalkyl ring or a $C_3$–$C_{12}$-cycloalkenyl ring, which optionally can be substituted in one or more places in the same way or differently with hydroxy, halogen, amino, $C_{1-6}$-alkoxy, or with the group —$NHC_{1-6}$-alkyl or —N-di-$C_{1-6}$-alkyl, or $R^5$ and $R^6$ optionally together form a double bond, T stands for —$CH_2$—, —O—, —$CH_2$=$CH_2$—, —CH≡CH—, —$CH_2$—O—$CH_2$—, —$CH_2$—O—, —O—$CH_2$— or =CO, and n stands for 0–6, as well as tautomers, isomers and salts thereof, have proven quite especially valuable.

Those compounds of general formula I, in which $R^1$ stands for linear or branched $C_1$–$C_6$-alkyl, $C_2$–$C_6$-alkenyl, $C_2$–$C_6$-alkinyl, $C_1$–$C_6$-alkoxy, $C_1$–$C_6$-alkylthio or cyclopropyl, cyclobutyl, cyclopentyl, cyclohexyl, cycloheptyl, cyclooctyl, cyclononyl, cyclodecyl, norbornyl, adamantanyl, cyclobutenyl, cyclopentenyl, cyclohexenyl, cycloheptenyl, cyclooctenyl, cyclononenyl or cyclodecenyl, oxiranyl, oxethanyl, aziridinyl, azetidinyl, tetrahydrofuranyl, pyrrolidinyl, dioxolanyl, imidazolidinyl, pyrazolidinyl, dioxanyl, piperidinyl, morpholinyl, dithianyl, thiomorpholinyl, piperazinyl, trithianyl, quinuclidinyl, pyrrolinyl, imidazolinyl, pyrazolinyl, pyranyl, thiinyl, dihydroazetyl, cyclopropenyl, cyclopentadienyl, phenyl, tropyl, cyclooctadienyl, indenyl, naphthyl, biphenyl, azulenyl, fluorenyl, anthracenyl, thienyl, furanyl, pyrrolyl, oxazolyl, thiazolyl, imidazolyl, pyrazolyl, isoxazolyl, isothiazolyl, oxadiazolyl, triazolyl, thiadiazolyl, benzofuranyl, benzothienyl, pyridyl, pyridazinyl, pyrimidinyl, pyrazinyl, triazinyl, oxepinyl, azocinyl, indolizinyl, indolyl, isoindolyl, indazolyl, benzimidazolyl, purinyl, quinolinyl, isoquinolinyl, cinnolinyl, phthalazinyl, quinazolinyl, quinoxalinyl, naphthyridinyl, pteridinyl, carbazolyl, acridinyl, phenazinyl, phenothiazinyl, 1,3-benzodioxol-5-yl, phenoxazinyl or xanthenyl, which optionally can be substituted in one or more places in the same way or differently with hydroxy, halogen, amino, $C_6$-alkyl, $C_{1-16}$-alkoxy, $C_{1-6}$-alkylthio, halo-$C_{1-6}$-alkyl, halo-$C_{1-6}$-alkoxy, $C_{1-6}$-alkoxycarbonyl, cyano, nitro, $C_{1-6}$-alkylsulfanyl, $C_{1-6}$-alkylsulfinyl, $C_{1-6}$-alkylsulfonyl, or can be substituted with the group —C(O)$C_{1-6}$-alkyl, —$NHC_{1-6}$-alkyl, —N-di-$C_{1-6}$-alkyl, —$CONH_2$, —$CONHC_{1-6}$-alkyl or —CON-di-$C_{1-6}$-alkyl, or can be substituted with another aryl or heteroaryl radical, which optionally itself can be substituted in one or more places in the same way or differently with hydroxy, halogen, amino, $C_{1-6}$-alkyl, $C_{1-6}$-alkoxy, $C_{1-6}$-alkylthio, halo-$C_{1-6}$-alkyl, halo-$C_{1-6}$-alkoxy, $C_{1-6}$-alkoxycarbonyl, cyano, nitro, $C_{1-6}$-alkylcarbonyl, $C_{1-6}$-alkylsulfanyl, $C_{1-6}$-alkylsulfinyl, $C_{1-6}$-alkylsulfonyl, or with the group —C(O)$C_{1-6}$- alkyl, —NHC$_{1-6}$-alkyl, —N-di-C$_{1-6}$-alkyl, —CONH$_2$, —CONHC$_{1-6}$-alkyl or —CON-di-C$_{1-6}$-alkyl, R$^2$ and R$^3$ are the same or different and stand for hydrogen, linear or branched C$_1$–C$_6$-alkyl, C$_2$–C$_6$-alkenyl, C$_2$–C$_6$-alkinyl or C$_1$–C$_6$-alkoxy, which optionally can be substituted in one or more places in the same way or differently with hydroxy, halogen, amino, C$_{1-6}$-alkoxy, or with the group —NHC$_{1-6}$-alkyl or —N-di-C$_{1-6}$-alkyl, R$^4$ and R$^5$ are the same or different and stand for hydrogen, halogen, linear or branched C$_1$–C$_6$-alkyl, C$_2$–C$_6$-alkenyl, C$_2$–C$_6$-alkinyl or C$_1$–C$_6$-alkoxy, which optionally can be substituted in one or more places in the same way or differently with hydroxy, halogen, amino, C$_{1-6}$-alkoxy, or with the group —NHC$_{1-6}$-alkyl or —N-di-C$_{1-6}$-alkyl, or together stand for a carbonyl group, or together form a cyclic five- or six-ring-acetal of the structure

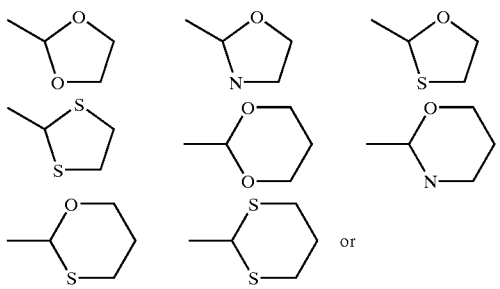

R$^2$ and R$^4$ together form a C$_3$–C$_7$-cycloalkyl ring or a C$_3$–C$_7$-cycloalkenyl ring, which optionally can be substituted in one or more places in the same way or differently with hydroxy, halogen, amino, C$_{1-6}$-alkoxy, or with the group —NHC$_{1-6}$-alkyl or —N-di-C$_{1-6}$-alkyl, or R$^3$ and R$^5$ together form a C$_3$–C$_7$-cycloalkyl ring or a C$_3$–C$_7$-cycloalkenyl ring, which optionally can be substituted in one or more places in the same way of differently with hydroxy, halogen, amino, C$_{1-6}$-alkoxy, or with the group —NHC$_{1-6}$-alkyl or —N-di-C$_{1-6}$-alkyl, R$^6$ and R$^7$ are the same or different and stand for hydrogen, linear or branched C$_1$–C$_6$-alkyl, C$_2$–C$_6$-alkenyl or C$_2$–C$_6$-alkinyl, which optionally can be substituted in one or more places in the same way or differently with hydroxy, halogen, amino, C$_{1-6}$-alkoxy, or with the group —NHC$_{1-6}$-alkyl or —N-di-C$_{1-6}$-alkyl, or together form a C$_3$–C$_7$-cycloalkyl ring or a C$_3$–C$_7$-cycloalkenyl ring, which optionally can be substituted in one or more places in the same way or differently with hydroxy, halogen, amino, C$_{1-6}$-alkoxy, or with the group —NHC$_{1-6}$-alkyl or —N-di-C$_{1-6}$-alkyl, or R$^5$ and R$^6$ optionally together form a double bond, T stands for —CH$_2$—, —O—, —CH$_2$=CH$_2$—, —CH≡CH—, —CH$_2$—O—CH$_2$—, —CH$_2$—O—, —O—CH$_2$— or =CO, and n stands for 0–6, as well as tautomers, isomers and salts thereof, are especially valuable.

Selected compounds are those compounds of general formula I, in which

R$^1$ stands for C$_1$–C$_6$-alkylthio, phenyl, biphenyl, thienyl, cyclopropyl, cyclohexyl, pyridyl, naphthyl, 1,3-benzodioxol-5-yl or isoxazolyl, which optionally can be substituted in one or more places in the same way or differently with halogen, amino, cyano, C$_{1-6}$-alkylsulfonyl, C$_{1-6}$-alkyl, halo-C$_{1-6}$-alkyl, C$_{1-6}$-alkoxy, C$_{1-6}$-alkylthio, or with the group —C(O)C$_{1-6}$-alkyl, or which can be substituted with phenyl, thienyl, naphthyl, pyridyl, furanyl or pyrimidinyl, which optionally itself can be substituted in one or more places in the same way or differently with C$_{1-6}$-alkyl, C$_{1-6}$-alkoxy, amino, C$_{1-6}$-alkylsulfonyl, cyano or with the group —C(O)NH$_2$, R$^2$, R$^3$, R$^4$, R$^5$, R$^6$ and R$^7$ stand for hydrogen or C$_{1-6}$-alkyl, T stands for the group —CH$_2$—, —CH$_2$—O—CH$_2$— or —CH$_2$—O—, and n stands for 0–2, as well as tautomers, isomers and salts thereof.

The production of the compounds of general formula I according to the invention is preferably carried out by a) a 1,4,5,6-tetrahydro-cyclopentapyrazol-3-yl-amine of general formula II (II)

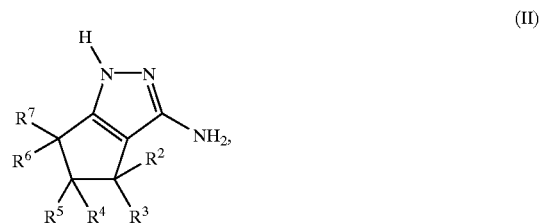

in which R$^2$, R$^3$, R$^4$, R$^5$, R$^6$ and R$^7$ have the meanings that are indicated in general formula I, being reacted with a compound of general formula III

R$^1$—COX (III), in which R$^1$ has the meaning that is indicated in general formula I, and X stands for hydroxy, fluorine, chlorine, bromine or a leaving group, to form compounds of general formulas IVa and IVb (IV a)

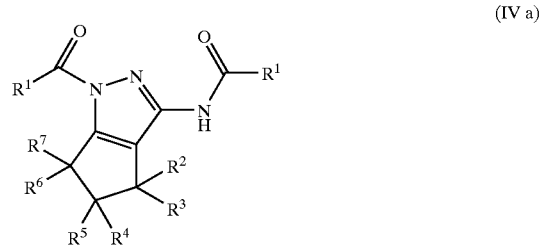

(IV b)

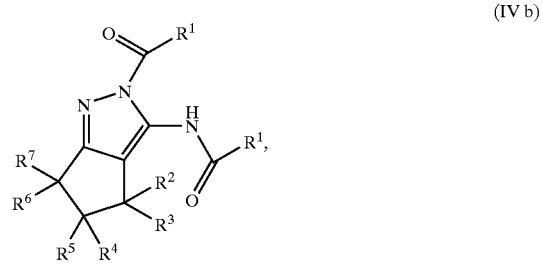

in which R$^1$ has the meaning that is indicated in general formula I, which then are hydrolyzed selectively under basic conditions to form the compounds of general formula I, or b) a 1,4,5,6-tetrahydro-cyclopentapyrazol-3-yl-amine of general formula II

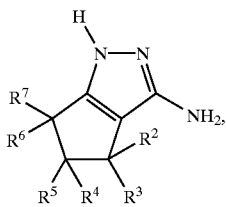
(II)

in which $R^2$, $R^3$, $R^4$, $R^5$, $R^6$ and $R^7$ have the meanings that are indicated in general formula I, being reacted with a compound of general formula V $R^1$—CO—$CCl_3$ (V), in which $R^1$ has the meaning that is indicated in general formula I, to form a compound of general formula I, or c) if $R^1$ stands for a 4-halophenylacetyl radical in the meaning of general formula I, a compound of general formulas VI or VI a

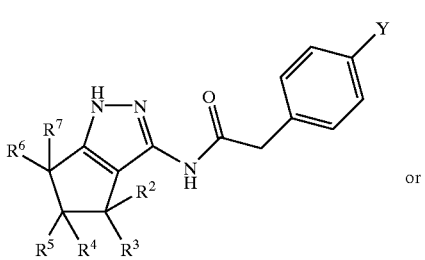
(VI)

or

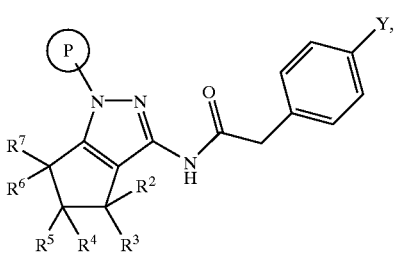
(VIa)

in which $R^2$, $R^3$, $R^4$, $R^5$, $R^6$ and $R^7$ have the meanings that are indicated in general formula I,

stands for a solid phase and Y stands for bromine or iodine, being reacted under the conditions of a Suzuki reaction with a boronic acid of general formula VII

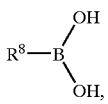
(VII)

in which $R^8$ stands for aryl or heteroaryl, to form a compound of general formula Ia or Ib,

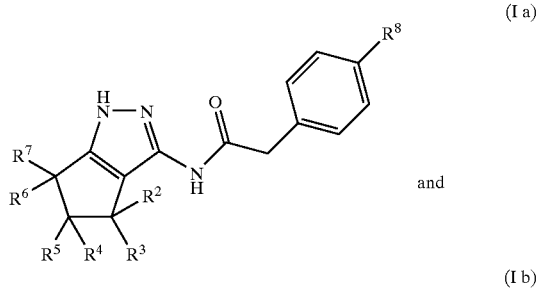
(Ia)

and (Ib)

in which $R^2$, $R^3$, $R^4$, $R^5$, $R^6$ and $R^7$ have the meanings that are indicated in general formula I, $R^8$ stands for aryl or heteroaryl, and

means a solid phase, whereby in the case of the compound that is bonded to a solid phase, the cleavage is carried out by acid hydrolysis, or d) a compound of general formula VI or VIa, in which $R^1$ stands for a 4-halophenylacetyl radical,

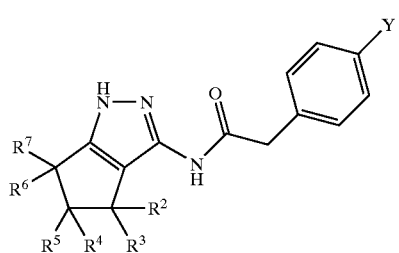
(VI)

or

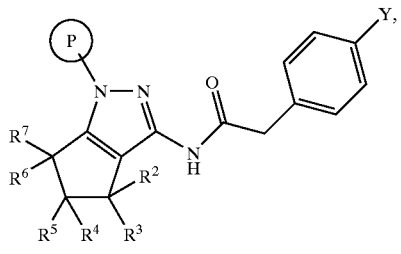
(VIa)

in which $R^2$, $R^3$, $R^4$, $R^5$, $R^6$ and $R^7$ have the meanings that are indicated in general formula I,

means a solid phase, and Y stands for bromine or iodine, being reacted under the conditions of a Miyaura reaction with a diboronic acid derivative of general formula VIII

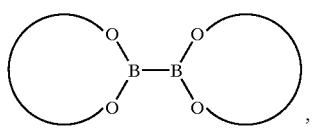

(VIII)

to form compounds of general formulas IX or IX a

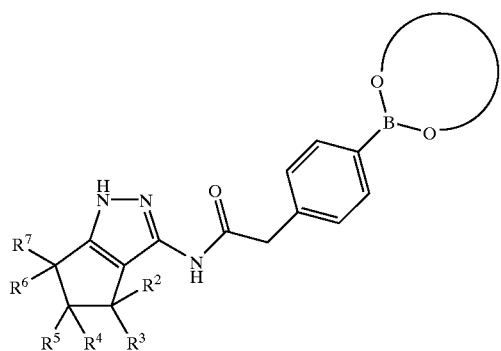

(IX)

or (IXa)

in which $R^2$, $R^3$, $R^4$, $R^5$, $R^6$ and $R^7$ have the meanings that are indicated in general formula I, and

means a solid phase, and then the compounds of general formulas IX and IXa being reacted with a compound of general formula X, $$R^9Z \quad (X),$$

in which $R^9$ stands for aryl or heteroaryl and Z stands for bromine or iodine, to form compounds of general formulas Ic or Id

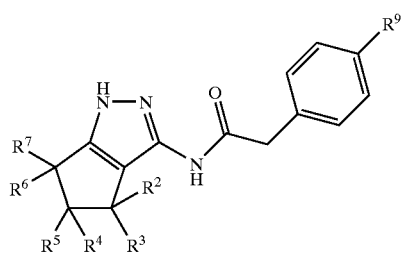

(Ic)

or

-continued

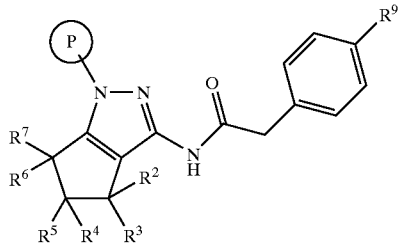

(Id)

in which $R^2$, $R^3$, $R^4$, $R^5$, $R^6$ and $R^7$ have the meanings that are indicated in general formula I,

means a solid phase, and $R^9$ stands for aryl or heteroaryl, and in the case of the compound that is bonded to a solid phase, the cleavage is carried out by acidic hydrolysis, or e) a compound of general formula XI

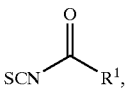

(XI)

in which $R^1$ has the meanings that are indicated in general formula I, being reacted with N-(1-cyclopenten-1-yl)-morpholine of general formula XII

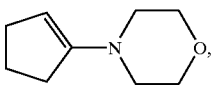

(XII)

to form compounds of general formula XIII

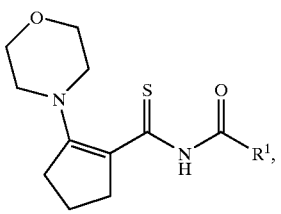

(XIII)

in which $R^1$ has the meanings that are indicated in general formula I, and then the compounds of general formula XIII being cyclized with hydrazine to compounds of formula I, or f) a compound of general formula XIV,

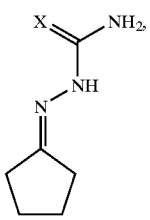

(XIV)

in which X stands for oxygen or sulfur, being reacted with a compound of general formula XV in the presence of strong bases (e.g., lithium diisopropylamide), $$R^1-COOR^{10}$$ (XV), in which $R^1$ has the meaning that is indicated in general formula I, and $R^{10}$ stands for $C_1-C_6$-alkyl, to form a compound of general formula I.

Process Variant a)

The reaction of 1,4,5,6-tetrahydro-cyclopentapyrazol-3-yl-amine of formula II with a compound of formula III can be carried out in the presence of a base such as triethylamine, N-methylmorpholine, N,N-diisopropylethylamine or pyridine in a suitable solvent, such as toluene, dichloromethane, chloroform, diethyl ether, tetrahydrofuran, acetonitrile, dioxane or N,N-dimethylformamide at a temperature of between 0° C. and the boiling point of the solvent. One of the methods, known from peptide chemistry, for forming amides can also be used.

The reaction of a compound of general formula IVa and IVb to form a compound of formula I can be carried out in the presence of a base such as sodium hydroxide, potassium hydroxide, sodium carbonate, potassium carbonate or sodium methylate in a suitable solvent, such as methanol, ethanol or a mixture that consists of methanol or ethanol with water at room temperature.

Process Variant b)

The reaction of 1,4,5,6-tetrahydro-cyclopentapyrazol-3-yl-amine of formula II with a compound of formula V to form a compound of formula I can be carried out in the presence of a base such as triethylamine, N-methylmorpholine, N,N-diisopropyl ethylamine in a suitable solvent, such as tetrahydrofuran, acetonitrile, dioxane or N,N-dimethylformamide at a temperature of between room temperature and the boiling point of the solvent.

Process Variant c)

The Suzuki reaction of a compound of formula VI with a boronic acid of formula VII can be carried out in the presence of a base such as cesium fluoride, sodium carbonate or potassium carbonate and a catalyst such as $Pd(PPh_3)_4$, $PdCl_2(PPh_3)_2$, or $Pd(OAc)_2/PPh_3$ in a suitable solvent such as dioxane, tetrahydrofuran, dimethoxyethane or a mixture that consists of methanol and dimethoxyethane at a temperature of between room temperature and the boiling point of the solvent.

Process Variant d)

The Miyaura reaction of a compound of formula VI with a diboronic acid derivative of formula VIII to form a compound of formula IX can be carried out in the presence of a base, such as potassium acetate or triethylamine and a catalyst such as $PdCl_2$ (diphenylphosphinoferrocene) or $PdCl_2(PPh_3)_2$ in a suitable solvent such as acetonitrile, dioxane, dimethoxyethane, dimethyl sulfoxide or N,N-dimethylformamide at a temperature of between room temperature and the boiling point of the solvent.

The reaction of a compound of formula IX with a compound of formula X can be carried out in the presence of a base such as sodium carbonate, potassium carbonate or potassium phosphate and a catalyst such as $Pd(PPh_3)_4$ or $PdCl_2(PPh_3)_2$ in a suitable solvent such as dioxane, tetrahydrofuran, dimethoxyethane or N,N-dimethylformamide at a temperature of between room temperature and the boiling point of the solvent.

Process Variant e)

The reaction of a compound of formula XI with N-(1-cyclopenten-1-yl)-morpholine of formula XII to form a compound of formula XIII can be carried out in a suitable solvent such as petroleum ether, ligroin, cyclohexane, hexane, pentane, acetonitrile or dichloromethane at a temperature of between room temperature and the boiling point of the solvent.

The reaction of a compound of formula XIII with hydrazine or hydrazine hydrate can be carried out in a suitable solvent such as methanol, ethanol or tetrahydrofuran at a temperature of between room temperature and the boiling point of the solvent.

Process Variant f)

The reaction of a compound of formula XIV with a compound of formula XV to form a compound of formula I can be carried out analogously to what is described in J. Heterocyclic Chem. 34, 1549 (1997).

The 1,4,5,6-tetrahydro-cyclopentapyrazol-3-yl-amine of formula II is new and can be obtained according to the methods that are described in the literature, e.g., from cyclopentanone thiosemicarbazone (J. Heterocyclic Chem. 34, 1549 (1997)) or from cyclopentanone-2-carbonitrile (J. Org. Chem., 52, 5538 (1987)).

Subjects of this invention are thus also compounds of general formula II,

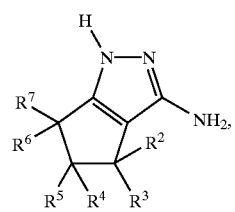

(II)

in which $R^2$, $R^3$, $R^4$, $R^5$, $R^6$ and $R^7$ have the meanings that are indicated in general formula I, as valuable intermediate products for the production of the compounds of general formula I according to the invention.

The compounds of formulas III, V, VII, VIII, X, XI, XII, XIV and XV are either commercially available or can be produced according to methods that are known in the literature.

The compounds of formula I and the precursors for their production that are bonded to the solid phase can be produced according to methods that are known in the art. Also, the cleavage can be performed by acid hydrolysis to form the free compounds according to the known methods.

The compounds according to the invention essentially inhibit cyclin-dependent kinases, upon which their action is based, for example, against cancer, such as solid tumors and leukemia; auto-immune diseases, such as psoriasis, alopecia and multiple sclerosis; chemotherapy agent-induced alopecia and mucositis; cardiovascular diseases, such as stenoses, arterioscleroses and restenoses; infectious diseases, such as, e.g., those caused by unicellular parasites, such as trypanosoma, toxoplasma or plasmodium, or those caused by fungi; nephrological diseases, such as, e.g., glomerulonephritis; chronic neurodegenerative diseases, such as Huntington's disease, amyotrophic lateral sclerosis, Parkinson's disease, AIDS dementia and Alzheimer's disease; acute neurodegenerative diseases, such as ischemias of the brain and neurotraumas; viral infections, such as, e.g., cytomegalic infections, herpes, Hepatitis B and C, and HIV diseases.

This invention thus also relates to the use of compounds according to the invention in these indications.

Figure 1:
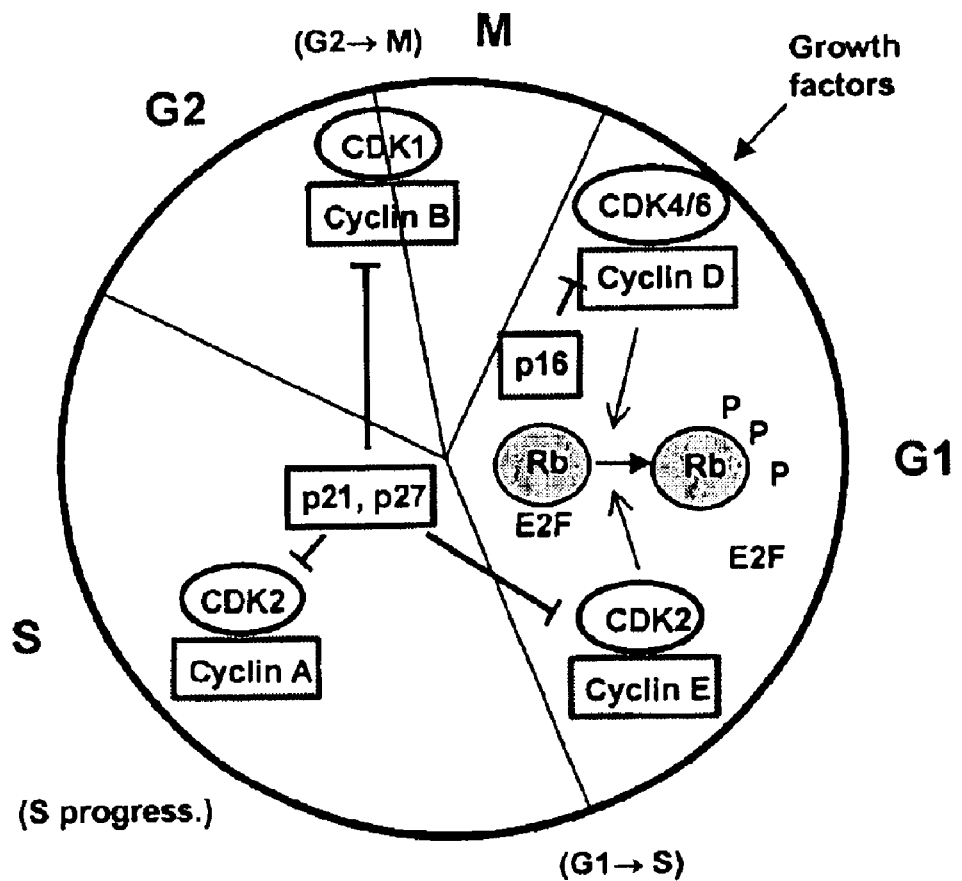
FIG. 1 provides a schematic of the cell-division cycle and means for its regulation and control as discussed herein.

The eukaryotic cell-division cycle ensures the duplication of the genome and its dispersion to the daughter cells by passing through a coordinated and regulated sequence of events. The cell cycle is divided into four successive phases: The G1 phase represents the time before the DNA replication in which the cell grows and is sensitive to external stimuli. In the S phase, the cell replicates its DNA, and in the G2 phase, preparations are made for entry into mitosis. In the mitosis (M phase), the replicated DNA is separated, and the cell division is completed.

The cyclin-dependent kinases (CDKs), a family of Ser/Thr-kinases, whose members require the binding of a cyclin (Cyc) as a regulatory subunit in order for them to activate, drive the cell through the cell cycle. Different CDK/Cyc pairs are active in the various phases of the cell cycle. CDK/Cyc pairs that are important to the basic function of the cell cycle are, for example, CDK4(6)/CycD, CDK2/CycE, CDK2/CycA, CDK1/CycA and CDK1/CycB. Some members of the CDK enzyme family have a regulatory function by influencing the activity of the above-mentioned cell cycle CDKs, while no specific function could be associated with other members of the CDK enzyme family. One of the latter, CDK5, is distinguished in that it has an a typical regulatory subunit (p35) that deviates from the cyclins, and its activity is highest in the brain.

The entry into the cell cycle and the passage through the "restriction points," which marks the independence of a cell from further growth signals for the completion of the cell division that has begun, are controlled by the activity of the CDK4(6)/CycD and CDK2/CycE complexes. The essential substrate of these CDK complexes is the retinoblastoma protein (Rb), the product of the retinoblastoma tumor suppressor gene. Rb is a transcriptional co-repressor protein. In addition to other, still largely little understood mechanisms, Rb binds and inactivates transcription factors of the E2F type and forms transcriptional repressor complexes with histone-deacetylases (HDAC) (Zhang, H. S. et al. (2000). Exit from G1 and S Phase of the Cell Cycle is Regulated by Repressor Complexes Containing HDAC-Rb-hSWI/SNF and Rb-hSWI/SNF. Cell 101, 79–89). By the phosphorylation of Rb by CDKs, bonded E2F transcription factors are released and result in transcriptional activation of genes, whose products are required for the DNA synthesis and the progression through the S-phase. In addition, the Rb-phosphorylation brings about the breakdown of the Rb-HDAC complexes, by which additional genes are activated. The phosphorylation of Rb by CDK's is to be treated as equivalent to exceeding the "restriction points." For the progression through the S-phase and its completion, the activity of the CDK2/CycE and CDK2/CycA complexes is necessary, e.g., the activity of the transcription factors of the E2F type is turned off by means of phosphorylation by CDK2/CycA as soon as the cells are entered into the S-phase. After replication of DNA is complete, the CDK1 in the complex with CycA or CycB controls the entry into and the passage through phases G2 and M (FIG. 1).

According to the extraordinary importance of the cell-division cycle, the passage through the cycle is strictly regulated and controlled. The enzymes that are necessary for the progression through the cycle must be activated at the correct time and are also turned off again as soon as the corresponding phase is passed. Corresponding control points ("checkpoints") stop the progression through the cell cycle if DNA damage is detected, or the DNA replication or the creation of the spindle device is not yet completed.

The activity of the CDKs is controlled directly by various mechanisms, such as synthesis and degradation of cyclins, complexing of the CDKs with the corresponding cyclins, phosphorylation and dephosphorylation of regulatory Thr and Tyr radicals, and the binding of natural inhibitory proteins. While the amount of protein of the CDKs in a proliferating cell is relatively constant, the amount of the individual cyclins oscillates with the passage through the cycle. Thus, for example, the expression of CycD during the early G1 phase is stimulated by growth factors, and the expression of CycE is induced after the "restriction points" are exceeded by the activation of the transcription factors of the E2F type. The cyclins themselves are degraded by the ubiquitin-mediated proteolysis. Activating and inactivating phosphorylations regulate the activities of the CDKs, for example phosphorylate CDK-activating kinases (CAKs) Thr160/161 of the CDK1, while, by contrast, the families of Wee1/Myt1 inactivate kinases CDK1 by phosphorylation of Thr14 and Tyr15. These inactivating phosphorylations can be destroyed in turn by cdc25 phosphatases. The regulation of the activity of the CDK/Cyc complexes by two families of natural CDK inhibitor proteins (CKIs), the protein products of the p21 gene family (p21, p27, p57) and the p16 gene family (p15, p16, p18, p19) is very significant. Members of the p21 family bind to cyclin complexes of CDKs 1,2,4,6, but inhibit only the complexes that contain CDK1 or CDK2. Members of the p 16 family are specific inhibitors of the CDK4 and CDK6 complexes.

The plane of control point regulation lies above this complex direct regulation of the activity of the CDKs. Control points allow the cell to track the orderly sequence of the individual phases during the cell cycle. The most important control points lie at the transition from G1 to S and from G2 to M. The G1 control point ensures that the cell does not initiate any DNA synthesis unless it has proper nutrition, interacts correctly with other cells or the substrate, and its DNA is intact. The G2/M control point ensures the complete replication of DNA and the creation of the mitotic spindle before the cell enters into mitosis. The G1 control point is activated by the gene product of the p53 tumor suppressor gene. p53 is activated after detection of changes in metabolism or the genomic integrity of the cell and can trigger either a stopping of the cell cycle progression or apoptosis. In this case, the transcriptional activation of the expression of the CDK inhibitor protein p21 by p53 plays a decisive role. A second branch of the G1 control point comprises the activation of the ATM and Chk1 kinases after DNA damage by UV light or ionizing radiation and finally the phosphorylation and the subsequent proteolytic degradation of the cdc25A phosphatase (Mailand, N. et al. (2000). Rapid Destruction of Human cdc25A in Response to DNA Damage. Science 288, 1425–1429). A shutdown of the cell cycle results from this, since the inhibitory phosphorylation of the CDKs is not removed. After the G2/M control point is activated by damage of the DNA, both mechanisms are involved in a similar way in stopping the progression through the cell cycle.

The loss of the regulation of the cell cycle and the loss of function of the control points are characteristics of tumor cells. The CDK-Rb signal path is affected by mutations in over 90% of human tumor cells. These mutations, which finally result in inactivating phosphorylation of the RB, include the over-expression of D- and E-cyclins by gene amplification or chromosomal translocations, inactivating mutations or deletions of CDK inhibitors of the p16 type, as well as increased (p27) or reduced (CycD) protein degradation. The second group of genes, which are affected by mutations in tumor cells, codes for components of the control points. Thus p53, which is essential for the G1 and G2/M control points, is the most frequently mutated gene in human tumors (about 50%). In tumor cells that express p53 without mutation, it is often inactivated because of a greatly increased protein degradation. In a similar way, the genes of other proteins that are necessary for the function of the control points are affected by mutations, for example ATM (inactivating mutations) or cdc25 phosphatases (overexpression).

Convincing experimental data indicate that CDK2/Cyc complexes occupy a decisive position during the cell cycle progression: (1) Both dominant-negative forms of CDK2, such as the transcriptional repression of the CDK2 expression by anti-sense oligonucleotides, produce a stopping of the cell cycle progression. (2) The inactivation of the CycA gene in mice is lethal. (3) The disruption of the function of the CDK2/CycA complex in cells by means of cell-permeable peptides resulted in tumor cell-selective apoptosis (Chen, Y. N. P. et al. (1999). Selective Killing of Transformed Cells by Cyclin/Cyclin-Dependent Kinase 2 Antagonists. Proc. Natl. Acad. Sci. USA 96, 4325–4329).

Changes of the cell cycle control play a role not only in carcinoses. The cell cycle is activated by a number of viruses, both by transforming viruses as well as by non-transforming viruses, to make possible the reproduction of viruses in the host cell. The false entry into the cell cycle of normally post-mitotic cells is associated with various neurodegenerative diseases. The mechanisms of the cell cycle regulation, their changes in diseases and a number of approaches to develop inhibitors of the cell cycle progression and especially the CDKs were already described in a detailed summary in several publications (Sielecki, T. M. et al. (2000). Cyclin-Dependent Kinase Inhibitors: Useful Targets in Cell Cycle Regulation. J. Med. Chem. 43, 1–18; Fry, D. W. & Garrett, M. D. (2000). Inhibitors of Cyclin-Dependent Kinases as Therapeutic Agents for the Treatment of Cancer. Curr. Opin. Oncol. Endo. Metab. Invest. Drugs 2, 40–59; Rosiania, G. R. & Chang, Y. T. (2000). Targeting Hyperproliferative Disorders with Cyclin-Dependent Kinase Inhibitors. Exp. Opin. Ther. Patents 10, 215–230; Meijer L. et al. (1999). Properties and Potential Applications of Chemical Inhibitors of Cyclin-Dependent Kinases. Pharmacol. Ther. 82, 279–284; Senderowicz, A. M. & Sausville, E. A. (2000). Preclinical and Clinical Development of Cyclin-Dependent Kinase Modulators. J. Natl. Cancer Inst. 92, 376–387).

To use the compounds according to the invention as pharmaceutical agents, the latter are brought into the form of a pharmaceutical preparation, which in addition to the active ingredient for enteral or parenteral administration contains suitable pharmaceutical, organic or inorganic inert support media, such as, for example, water, gelatin, gum arabic, lactose, starch, magnesium stearate, talc, vegetable oils, polyalkylene glycols, etc. The pharmaceutical preparations can be present in solid form, for example as tablets, coated tablets, suppositories, or capsules, or in liquid form, for example as solutions, suspensions, or emulsions. Moreover, they optionally contain adjuvants, such as preservatives, stabilizers, wetting agents or emulsifiers; salts for changing the osmotic pressure or buffers.

These pharmaceutical preparations are also subjects of this invention.

For parenteral administration, especially injection solutions or suspensions, especially aqueous solutions of active compounds in polyhydroxyethoxylated castor oil, are suitable.

As carrier systems, surface-active adjuvants such as salts of bile acids or animal or plant phospholipids, but also mixtures thereof as well as liposomes or their components, can also be used.

For oral administration, especially tablets, coated tablets or capsules with talc and/or hydrocarbon vehicles or binders, such as, for example, lactose, corn or potato starch, are suitable. The administration can also be carried out in liquid form, such as, for example, as a juice, to which optionally a sweetener is added.

Enteral, parenteral and oral administrations are also subjects of this invention.

The dosage of the active ingredients can vary depending on the method of administration, age and weight of the patient, type and severity of the disease to be treated and similar factors. The daily dose is 0.5–1000 mg, preferably 50–200 mg, whereby the dose can be given as a single dose to be administered once or divided into two or more daily doses.

Subjects of this invention also include the use of compounds of general formula I for the production of a pharmaceutical agent for treating cancer, auto-immune diseases, cardiovascular diseases, chemotherapy agent-induced alopecia and mucositis, infectious diseases, nephrological diseases, chronic and acute neurodegenerative diseases and viral infections, whereby cancer is defined as solid tumors and leukemia; auto-immune diseases are defined as psoriasis, alopecia and multiple sclerosis; cardiovascular diseases are defined as stenoses, arteriscleroses and restenoses; infectious diseases are defined as diseases that are caused by unicellular parasites; nephrological diseases are defined as glomerulonephritis; chronic neurodegenerative diseases are defined as Huntington's disease, amyotrophic lateral sclerosis, Parkinson's disease, AIDS dementia and Alzheimer's disease; acute neurodegenerative diseases are defined as ischemias of the brain and neurotraumas; and viral infections are defined as cytomegalic infections, herpes, Hepatitis B or C, and HIV diseases.

Subjects of this invention also include pharmaceutical agents for treating the above-cited diseases, which contain at least one compound according to general formula I, as well as pharmaceutical agents with suitable formulation substances and vehicles.

The compounds of general formula I according to the invention are, i.a., excellent inhibitors of the cyclin-dependent kinases, such as CDK1, CDK2, CDK3, CDK4, CDK5, CDK6, CDK7, CDK8 and CDK9, as well as the glycogen-synthase-kinase (GSK-3β).

The following examples explain the production of the compounds according to the invention, without limiting the invention to these examples.

EXAMPLE 1.0

2-(3'-Fluoro-biphenyl-4-yl)-N-(1,4,5,6-tetrahydro-cyclopentapyrazol-3-yl)-acetamide 230 mg of 2-(3'-fluoro-biphenyl-4-yl)-acetic acid is dissolved in 5 ml of tetrahydrofuran, mixed with 0.11 ml of oxalyl chloride and one drop of dimethylformamide, and stirred for 2 hours at room temperature. 62 mg of 1,4,5,6-tetrahydro-cyclopentapyrazol-3-yl-amine is added to this solution. The mixture is stirred for 12 hours at room temperature and then concentrated by evaporation. The residue is extracted with ethyl acetate. The extract is washed with sodium bicarbonate solution and water, dried on magnesium sulfate and concentrated by evaporation. The brown residue is dissolved in 5 ml of methanol and mixed with 0.1 ml of a 30% sodium methylate solution. It is stirred for 4 hours at room temperature and then concentrated by evaporation. The residue is extracted with ethyl acetate. The extract is washed with sodium bicarbonate solution and sodium chloride solution, dried on magnesium sulfate and concentrated by evaporation. A yellow, resinous oil is obtained that is purified by HPLC. 2-(3'-Fluoro-biphenyl-4-yl)-N-(1,4,5,6-tetrahydro-cyclopentapyrazol-3-yl)-acetamide with a melting point of 180–181° C. is obtained.

Production of the Starting Material 1,4,5,6-Tetrahydro-cyclopentapyrazol-3-yl-amine 5.3 g of cyclopentanone thiosemicarbazone is carefully added at 0° C. to a solution of lithium diisopropylamine in 200 ml of tetrahydrofuran (from 29 ml of diisopropylamine and 81 ml of 1.6 M n-butyllithium), whereby the temperature rises to 30° C. Then, it is stirred for 2 hours at room temperature. Then, 150 ml of 4N hydrochloric acid is carefully added in drops (exothermic, H₂S development), and the mixture is refluxed for 30 minutes. Then, it is cooled to 5° C. and set at pH 14 with sodium hydroxide solution. The aqueous phase is extracted three times with tetrahydrofuran/ethyl acetate 95:5. The crude product is purified by column chromatography on silica gel with 1 l of ethyl acetate and 1 l of ethyl acetate/methanol 9:1 with the addition of 3% triethylamine. 2.58 g of 1,4,5,6-tetrahydro-cyclopentapyrazol-3-yl-amine with a melting point of 116–120° C. is obtained.

EXAMPLE 1.1

2-(Biphenyl-4-yl)-N-[6-methyl-(1,4,5,6-tetrahydro-cyclopentapyrazol-3-yl)]-acetamide The production of 2-(biphenyl-4-yl)-N-[6-methyl-(1,4,5,6-tetrahydro-cyclopentapyrazol-3-yl)]-acetamide is carried out analogously to Example 1.0.

Production of the Starting Material

6-Methyl-1,4,5,6-tetrahydro-cyclopentapyrazol-3-yl-amine

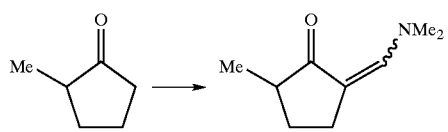

A mixture that consists of 1-methylcyclopentanone (9.82 g, 100 mmol) and dimethylformamide-dimethylacetal (26 ml, 150 mmol) is heated for 4.5 hours at 110° C., concentrated by evaporation and distilled in a ball-tube furnace at 160–170° C./2 mbar.
Yield: 7.7 g
MS-CI(NH3): 154

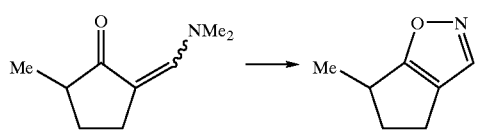

A solution of enamine (7.65 g, 50 mmol) in methanol (50 ml) is mixed with hydroxylamine-hydrochloride (3.47 g, 50 mmol), stirred for 1 hour at 50° C., mixed with diethyl ether, suctioned off, and the mother liquor is concentrated by evaporation.
Yield: 6.08 g isoxazole.
MS-EI: 124

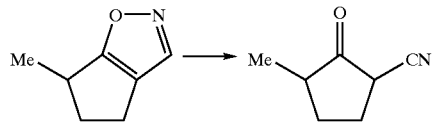

A solution of isoxazole (6.1 g, 50 mmol) in diethyl ether (100 ml) is mixed drop by drop with 0.5 M sodium methylate solution in methanol (100 ml, 50 mmol), and it is stirred for 24 hours at 23° C. The solution is concentrated by evaporation, the residue is cooled, mixed carefully with cold water, stirred with diethyl ether, and the organic phase is separated. The alkaline water phase is brought to pH 1 with 6N hydrochloric acid (12 ml), extracted with diethyl ether (4×40 ml), the organic phase is dried (Na₂SO₄), filtered off and concentrated by evaporation.
Yield: 4.6 g of 2-cyano-5-methylcyclopentanone.
MS-CI(NH3): 141
IR: 2240 cm−1 (CN), 1760 cm−1 (CO)

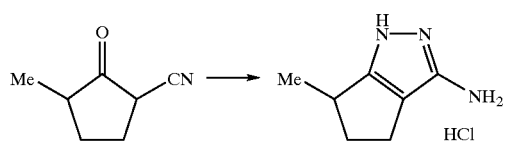

A solution of 2-cyano-5-methylcyclopentanone (1.23 g, 10 mmol) in ethanol (20 ml) is mixed at 23° C. with hydrazine hydrate (80% in water, 0.68 g, 10.8 mmol), and it is stirred for 2.5 hours at 23° C. 4N HCl-dioxane solution (2.5 ml, 10 mmol) is added into this solution, it is stirred for 1.5 hours at 23° C., concentrated by evaporation to half the volume, and the precipitated hydrochloride is suctioned off. The mother liquor is concentrated by evaporation, the residue is stirred in diethyl ether/ethanol, suctioned off and dried.
Yield: 780 mg of 6-methyl-1,4,5,6-tetrahydro-cyclopentapyrazol-3-yl-amine hydrochloride.
Melting point 191° C. (decomposition)
MS-CI(NH3): 138
1H-NMR (d6-DMSO): 13.6 (br.s, NH), 6.9 (br.s, NH2), 3.1 (sext., J≈7 Hz, 1H), 2.7–2.3 (m, 3H), 2.0–1.9 (m, 1H), 1.18 (d, J=6.7, 3H).

Similarly produced are also the following compounds:

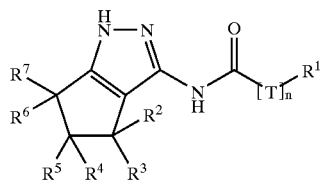

$R^2$, $R^3$, $R^4$, $R^5$, $R^6$ and $R^7$=hydrogen
T=—CH₂—

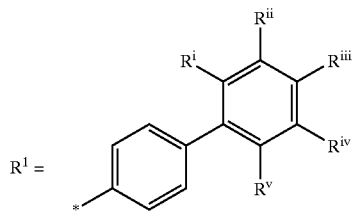

| Example No. | n | $R^i$ | $R^{ii}$ | $R^{iii}$ | $R^{iv}$ | $R^v$ | MW | Melting Point [°C] |
|---|---|---|---|---|---|---|---|---|
| 1.2 | 1 | H | H | F | H | H | 335.3802 | 161–163 |
| 1.3 | 1 | H | H | H | F | H | 335.3802 | 179–181 |
| 1.4 | 1 | H | H | H | H | —OCH$_3$ | 347.4159 | 150 |
| 1.5 | 1 | H | H | H | —OCH$_3$ | H | 347.4159 | 110–114 |
| 1.6 | 1 | H | H | —OCH$_3$ | H | H | 347.4159 | 168–172 |
| 1.7 | 1 | H | H | H | —C(O)CH$_3$ | H | 359.4269 | 150 |
| 1.8 | 1 | H | H | —C(O)CH$_3$ | H | H | 359.4269 | 112–114 |
| 1.9 | 1 | H | H | H | H | H | 317.39 | NMR (CDCl$_3$): m 2.42(2H), t 2.68 (4H), s3.71 (2H), d 7.34 (4H), t7.42 (1H), d7.57 (4H), sbr 8.36 (1H) |
| 1.10 | 1 | H | H | CN | H | H | 342.40 | 210 (dec.) |
| 1.11 | 1 | H | H | H | NH$_2$ | H | | |
| 1.12 | 1 | H | H | —SO$_2$CH$_3$ | H | H | | |

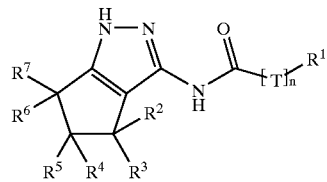

$R^2$, $R^3$, $R^4$, $R^5$, $R^6$ and $R^7$=hydrogen

T=—CH$_2$—

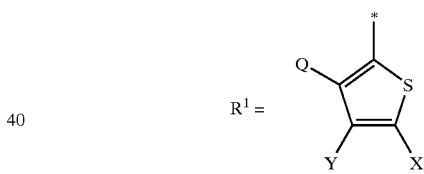

| Example No. | X | Y | Q | n | MW | Melting Point [°C] MS/NMR |
|---|---|---|---|---|---|---|
| 2.0 | H | H | H | 1 | 247.3207 | 248(100%, M + H); 150 (12%); 123 (24%) |

-continued

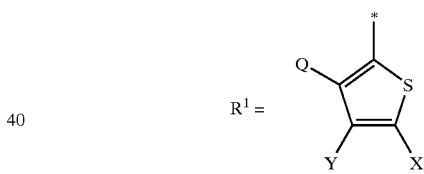

| Example No. | X | Y | Q | n | MW | Melting Point [°C] MS/NMR |
|---|---|---|---|---|---|---|
| 2.1 | H | H | H | 0 | 233.2939 | 234(100%, M + H); 204 (36%); 188 (12%); 124 (3%) |

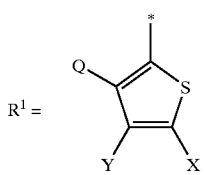

| Example No. | X | Y | n | MW | Melting Point [°C] MS/NMR |
|---|---|---|---|---|---|
| 3.0 | H | Ph | 0 | 267.3303 | 268(100%, M + H); 204 (43%); 188 (24%); 123 (11%) |

-continued

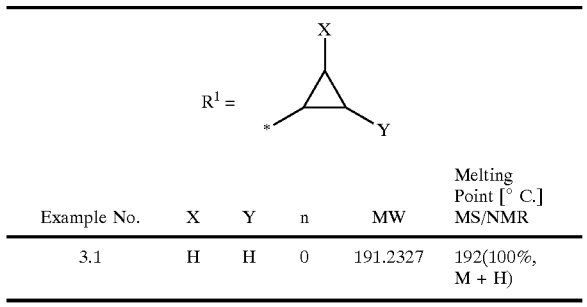

| Example No. | X | Y | n | MW | Melting Point [° C.] MS/NMR |
|---|---|---|---|---|---|
| 3.1 | H | H | 0 | 191.2327 | 192(100%, M + H) |

Ph = Phenyl $R^2$, $R^3$, $R^4$, $R^5$, $R^6$ and $R^7$=hydrogen

T=—CH$_2$—

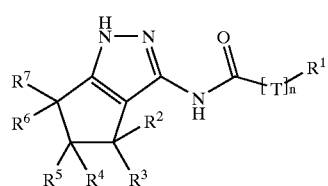

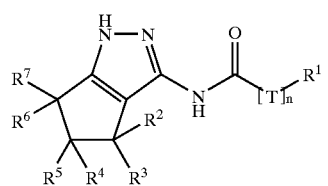

$R^2$, $R^3$, $R^4$, $R^5$, $R^6$ and $R^7$=hydrogen

T=—CH$_2$—

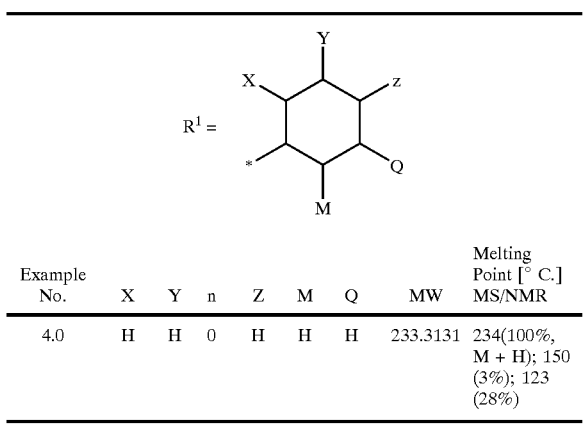

| Example No. | X | Y | n | Z | M | Q | MW | Melting Point [° C.] MS/NMR |
|---|---|---|---|---|---|---|---|---|
| 4.0 | H | H | 0 | H | H | H | 233.3131 | 234(100%, M + H); 150 (3%); 123 (28%) |

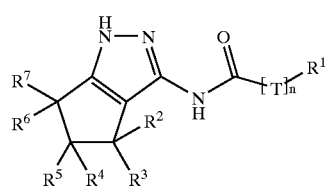

$R^2$, $R^3$, $R^4$, and $R^7$=hydrogen

T=—CH$_2$—

| Example No. | n | $R^1$ | MW | Melting Point [° C.] MS/NMR |
|---|---|---|---|---|
| 5.0 | 2 | —SCH$_3$ | 225.3145 | 226(100%, M + H); 204 (6%); 188 (3%); 150 (5%); 123 (22%) |
| 5.1 | 0 | 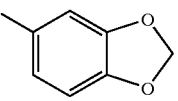 | 271.2747 | 272(100%, M + H); 204 (8%); 188 (5%); 149 (46%) |
| 5.2 | 0 | 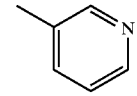 | 228.2538 | |
| 5.3 | 1 | 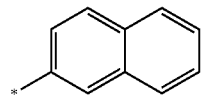 | 291.3523 | 176–178 |
| 5.4 | 0 | 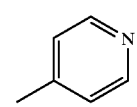 | 228.2538 | |

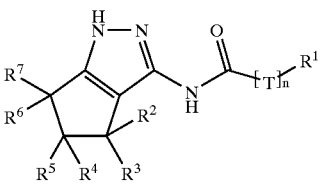

$R^2$, $R^3$, $R^4$, $R^5$, $R^6$ and $R^7$=hydrogen

T=—CH$_2$—

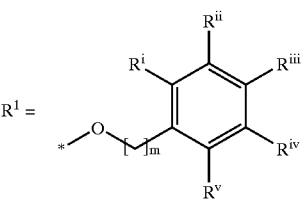

| Example No. | N | m | $R^i$ | $R^{ii}$ | $R^{iii}$ | $R^{iv}$ | $R^v$ | MW | Melting Point [° C.] MS/NMR |
|---|---|---|---|---|---|---|---|---|---|
| 6.0 | 1 | 1 | H | H | H | H | H | 271.3183 | 272(100%, M + H); 150 (3%); 123 (5%) |

-continued

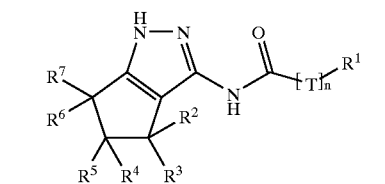

| Example No. | N | m | $R^i$ | $R^{ii}$ | $R^{iii}$ | $R^{iv}$ | $R^v$ | MW | Melting Point [° C.] MS/NMR |
|---|---|---|---|---|---|---|---|---|---|
| 6.1 | 1 | 0 | —$CH_3$ | H | Cl | H | H | 305.7634 | 306(100%, M + H); 150 (11%); 123 (21%) |

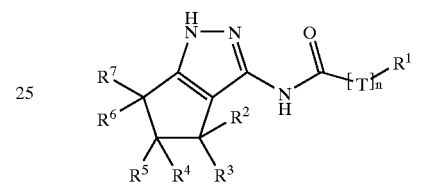

| Example No. | N | $R^x$ | $R^y$ | MW | Melting Point [° C.] MS/NMR |
|---|---|---|---|---|---|
| 7.0 | 0 | Ph | —$CH_3$ | 308.3394 | 309(100%, M + H); 204 (28%); 188(9%); 144 (15%); 124 (7%) |

Ph = Phenyl $R^2, R^3, R^4, R^5, R^6$ and $R^7$=hydrogen $R^2, R^3, R^4, R^5, R^6,$ and $R^7$=hydrogen
T=—$CH_2$—

| Example No. | X | Y | n | Z | M | Q | MW | Melting Point [° C.] MS/NMR |
|---|---|---|---|---|---|---|---|---|
| 8.0 | —$OCH_3$ | —$OCH_3$ | 1 | H | H | H | 301.3441 | 302(100%, M + H); 151(22%; 123(12%) |
| 8.1 | H | F | 1 | H | H | H | 259.2826 | 260(100%, M + H); 204(25%); 188 (18%); 150(11%); 123(34%) |
| 8.2 | —$OCH_3$ | H | 1 | H | H | H | 271.3183 | 272(100%, M + H); 204(7%); 124(9%) |
| 8.3 | H | H | 2 | H | H | H | 255.3193 | 256(100%), M + H); 204(29%); 188 (21%); 150(7%); 123 (53%) |
| 8.4 | H | —$OCH_3$ | 1 | H | H | H | 271.3183 | 272(100%, M + H); 148(12%); 121(19%) |
| 8.5 | H | H | 1 | H | H | H | 241.2925 | 242(100%, M + H); 150(8%); 123(30%) |
| 8.6 | H | H | 0 | H | H | H | 227.2657 | 228(100%, M + H); 204(6%); 187(8%) |
| 8.7 | —$OCH_3$ | H | 1 | H | —$OCH_3$ | H | 301.3441 | 302(100%), M + H |
| 8.8 | —$CF_3$ | H | 0 | H | H | H | 295.2628 | 296(100%, M + H); 204 (22%); 188(12%) |
| 8.9 | F | H | 0 | H | H | H | 245.2558 | 246(100%, M + H); 204(22%); 188 (12%); 123(25%) |
| 8.10 | H | —$OCH_3$ | 0 | H | H | H | 257.2915 | 258(100%, M + H); 204(40%); 188(15%) |

-continued
R¹ = 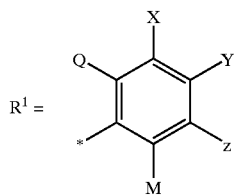
| Example No. | X | Y | n | Z | M | Q | MW | Melting Point [° C.] MS/NMR |
|---|---|---|---|---|---|---|---|---|
| 8.11 | H | I | 1 | H | H | H | 367.1846 | 180–181 |
| 8.12 | *-C₆H₅ | H | 1 | H | H | H | 317.3901 | 180–181 |
| 8.13 | Br | H | 1 | H | H | H | 320.1886 | 208–209 |
| 8.14 | H | Br | 1 | H | H | H | 320.1886 | 164–166 |
| 8.15 | H | —SCH₃ | 1 | H | H | H | 287.3853 | 164–166 |
| 8.16 | H | —C(CH₃)₃ | 1 | H | H | H | 297.40 | NMR(CDCl₃): s1.32(9H), m2.44 (2H), t2.69(4H), s3.70(2H), d7.22 (2H), d 7.40 (2H), sbr 7.81 (1H) |
| 8.17 | H | Cl | 1 | H | H | H | 275.7376 | NMR(CDCl₃): m2.43(2H), t2.68(4H), s3.61 (2H), d7.20(2H), d7.38(2H), sbr 8.53(1H) |
| 8.18 | H | *-C₆H₅ | 0 | H | H | H |  | 200 (decomposition) |
| 8.19 | H | *-thienyl | 1 | H | H | H | 323.42 | 217–218 |
| 8.20 | H | *-methylthienyl | 1 | H | H | H | 337.35 | 155–156 |
| 8.21 | H | *-naphthyl | 1 | H | H | H |  |  |
| 8.22 | H | *-dimethoxypyrimidinyl | 1 | H | H | H |  |  |
| 8.23 | H | *-pyridyl | 1 | H | H | H |  |  |

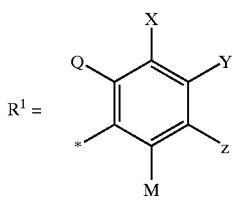
| Example No. | X | Y | n | Z | M | Q | MW | Melting Point [° C.] MS/NMR |
|---|---|---|---|---|---|---|---|---|
| 8.24 | H | *4-pyridyl | 1 | H | H | H | | |
| 8.25 | H | *3-furyl | 1 | H | H | H | | |
| 8.26 | *2-naphthyl | H | 1 | H | H | H | | 188 |
| 8.27 | *2,4-dimethoxypyrimidin-5-yl | H | 1 | H | H | H | | |
| 8.28 | *3-pyridyl | H | 1 | H | H | H | | |
| 8.29 | *4-pyridyl | H | 1 | H | H | H | | |
| 8.30 | *3-furyl | H | 1 | H | H | H | | |
| 8.31 | *3-aminophenyl | H | 1 | H | H | H | | |
| 8.32 | *4-methylsulfonylphenyl | H | 1 | H | H | H | | |
| 8.33 | *4-cyanophenyl | H | 1 | H | H | H | 342.40 | 173 |

-continued

R¹ = 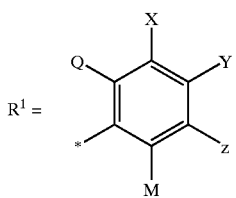

| Example No. | X | Y | n | Z | M | Q | MW | Melting Point [° C.] MS/NMR |
|---|---|---|---|---|---|---|---|---|
| 8.34 | *—⌬—CONH₂ | | H | 1 | H | H | H | 360.42 | 205 (dec.) |

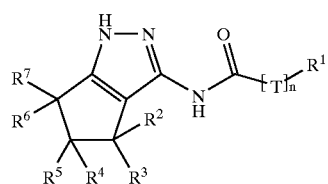

R², R³, R⁴, R⁵, R⁶ and R⁷=hydrogen
T=—CH(CH₃)—

R¹ =

| Example No. | N | $R^i$ | $R^{ii}$ | $R^{iii}$ | $R^{iv}$ | $R^v$ | MW | Melting Point [° C.] MS/NMR |
|---|---|---|---|---|---|---|---|---|
| 9.0 | 1 | H | H | H | H | H | 349.41 | 218–220 |

The following examples describe the biological action of the compounds according to the invention without limiting the invention to these examples.

Sample Application 1

CDK2/CycE Kinase Assay

Recombinant CDK2- and CycE-GST-fusion proteins, purified from baculovirus-infected insect cells (Sf9), were obtained by Dr. Dieter Marmé, Klinik für Tumorbiologie [Clinic for Tumor Biology], Freiburg. Histone IIIS, which was used as a kinase substrate, was purchased by the Sigma Company.

CDK2/CycE (50 ng/measuring point) was incubated for 15 minutes at 22° C. in the presence of various concentrations of test substances (0 μm, as well as within the range of 0.01–100 μm) in assay buffer [50 mmol of tris/HCl pH 8.0, 10 mmol of MgCl₂, 0.1 mmol of Na ortho-vanadate, 1.0 mmol of dithiothreitol, 0.5 μm of adenosine triphosphate (ATP), 10 μg/measuring point of histone IIIS, 0.2 μCi/measuring point of ³³P-gamma ATP, 0.05% NP40, 12.5% dimethyl sulfoxide]. The reaction was stopped by adding EDTA solution (250 mmol pH 8.0, 14 μl/measuring point).

From each reaction batch, 10 μl was applied to P30 filter strips (Wallac Company), and non-incorporated ³³P-ATP was removed by subjecting the filter strips to three washing cycles for 10 minutes each in 0.5% phosphoric acid. After the filter strips were dried for one hour at 70° C., the filter strips were covered with scintillator strips (MeltiLex™ A, Wallac Company) and baked for one hour at 90° C. The amount of incorporated ³³P (substrate phosphorylation) was determined by scintillation measurement in a gamma-radiation measuring device (Wallac).

Sample Application 2

Proliferation Assay

Cultivated human MCF7 tumor cells were flattened out at a density of 5000 cells/measuring point in a 96-well multi-titer plate in 200 μl of the corresponding growth medium. After 24 hours, the cells of one plate (zero-point plate) were colored with crystal violet (see below), while the medium of the other plates was replaced by fresh culture medium (200 μl), to which the test substances were added in various concentrations (0 μm, as well as in the range of 0.01–30 μm; the final concentration of the solvent dimethyl sulfoxide was 0.5%). The cells were incubated for 4 days in the presence of test substances. The cell proliferation was determined by coloring the cells with crystal violet: the cells were fixed by adding 20 μl/measuring point of a 11% glutaric aldehyde solution for 15 minutes at room temperature. After three washing cycles of the fixed cells with water, the plates were dried at room temperature. The cells were colored by adding 100 μl/measuring point of a 0.1% crystal violet solution (pH was set at 3 by adding acetic acid). After three washing cycles of the colored cells with water, the plates were dried at room temperature. The dye was dissolved by adding 100 μl/measuring point of a 10% acetic acid solution. The extinction was determined by photometry at a wavelength of 595 nm. The change of cell growth, in percent, was calculated by standardization of the measured values to the extinction values of the zero-point plate (=0%) and the extinction of the untreated (0 μm) cells (=100%).

| Example No. | CDK2/CycE IC$_{50}$ [M] |
|---|---|
| 1.0 | 7.0 |
| 1.2 | <10.0 |
| 1.3 | 7.0 |
| 1.4 | <10.0 |
| 1.5 | <10.0 |
| 1.6 | <10.0 |
| 1.7 | 4.3 |
| 1.8 | 6.5 |
| 1.9 | 1.0 |
| 2.0 | 4.0 |
| 2.1 | 4.0 |
| 3.1 | 4.0 |
| 5.1 | 4.0 |
| 8.1 | 3.0 |
| 8.2 | 7.6 |
| 8.3 | 3.0 |
| 8.4 | 0.7 |
| 8.5 | 1.5 |
| 8.6 | 7.0 |
| 8.7 | 5.2 |
| 8.9 | 5.0 |
| 8.10 | 6.0 |
| 8.11 | 0.8 |
| 8.12 | 8.0 |
| 8.13 | 1.5 |
| 8.14 | 1.1 |
| 8.15 | 1.5 |
| 8.16 | 1.0 |
| 8.17 | 1.5 |

What is claimed is:

1. Compounds of general formula I,

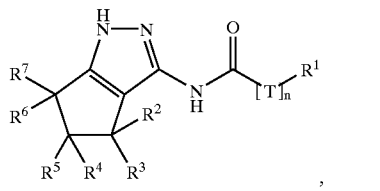

(I)

wherein $R^1$ stands for linear or branched $C_1$–$C_6$-alkyl, $C_2$–$C_6$-alkenyl, $C_2$–$C_6$-alkinyl, $C_1$–$C_6$-alkoxy, $C_1$–$C_6$-alkylthio or $C_3$–$C_{12}$-cycloalkyl, $C_3$–$C_{12}$-cycloalkenyl, $C_3$–$C_{12}$-heterocycloalkyl, $C_3$–$C_{12}$-heterocycloalkenyl, aryl or heteroaryl, which optionally can be substituted, $R^2$ and $R^3$ are the same or different and stand for hydrogen, linear or branched $C_1$–$C_6$-alkyl, $C_2$–$C_6$-alkenyl, $C_2$–$C_6$-alkinyl or $C_1$–$C_6$-alkoxy, which optionally can be substituted, $R^4$ and $R^5$ are the same or different and stand for hydrogen, halogen, linear or branched $C_1$–$C_6$-alkyl, $C_2$–$C_6$-alkenyl, $C_2$–$C_6$-alkinyl or $C_1$–$C_6$-alkoxy, which optionally can be substituted, or together stand for a carbonyl group, or together form a cyclic five- or six-ring-acetal with O,O; N,O; O,S; or S,S, which optionally can be substituted with $C_1$–$C_6$-alkyl, or $R^2$ and $R^4$ together form a $C_3$–$C_{12}$-cycloalkyl ring or a $C_3$–$C_{12}$-cycloalkenyl ring, which optionally can be substituted, $R^6$ and $R^7$ are the same or different and stand for hydrogen, linear or branched $C_1$–$C_6$-alkyl, $C_2$–$C_6$-alkenyl or $C_2$–$C_6$-alkinyl, which optionally can be substituted, or together form a $C_3$–$C_{12}$-cycloalkyl ring or a $C_3$–$C_{12}$-cycloalkenyl ring, which optionally can be substituted, or $R^5$ and $R^6$ optionally together form a double bond, or $R^3$ and $R^5$ together form a $C_3$–$C_{12}$-cycloalkyl ring or a $C_3$–$C_{12}$-cycloalkenyl ring, which optionally can be substituted, T stands for —CH$_2$—, —O—, —CH$_2$═CH$_2$—, —CH≡CH—, —CH$_2$—O—CH$_2$—, —CH$_2$—O—, —O—CH$_2$— or ═CO, and n stands for 0–6, or a tautomer, isomer or salt thereof.

2. A compounds of general formula I, according to claim 1, wherein $R^1$ stands for linear or branched $C_1$–$C_6$-alkyl, $C_2$–$C_6$-alkenyl, $C_2$–$C_6$-alkinyl, $C_1$–$C_6$-alkoxy, $C_1$–$C_6$-alkylthio or $C_3$–$C_{12}$-cycloalkyl, $C_3$–$C_{12}$-cycloalkenyl, $C_3$–$C_{12}$-heterocycloalkyl, $C_3$–$C_{12}$-heterocycloalkenyl, aryl or heteroaryl, which optionally can be substituted with hydroxy, halogen, amino, $C_{1-6}$-alkyl, $C_{1-6}$-alkoxy, $C_{1-6}$-alkylthio, halo-$C_{1-6}$-alkyl, halo-$C_{1-6}$-alkoxy, $C_{1-6}$-alkoxycarbonyl, cyano, nitro, $C_{1-6}$-alkylsulfanyl, $C_{1-6}$-alkylsulfinyl, $C_{1-6}$-alkylsulfonyl, or with the group —C(O)C$_{1-6}$-alkyl, —NHC$_{1-6}$-alkyl, —N-di-C$_{1-6}$-alkyl, —CONH$_2$, —CONHC$_{1-6}$-alkyl or —CON-di-C$_{1-6}$-alkyl, or can be substituted with another aryl radical or heteroaryl radical that optionally itself can be substituted, $R^2$ and $R^3$ are the same or different and stand for hydrogen, linear or branched $C_1$–$C_6$-alkyl, $C_2$–$C_6$-alkenyl, $C_2$–$C_6$-alkinyl or $C_1$–$C_6$-alkoxy, which optionally can be substituted with hydroxy, halogen, amino, $C_{1-6}$-alkoxy, or with the group —NHC$_{1-6}$-alkyl or —N-di-C$_{1-6}$-alkyl, $R^4$ and $R^5$ are the same or different and stand for hydrogen, halogen, linear or branched $C_1$–$C_6$-alkyl, $C_2$–$C_6$-alkenyl, $C_2$–$C_6$-alkinyl or $C_1$–$C_6$-alkoxy, which optionally can be substituted with hydroxy, halogen, amino, $C_{1-6}$-alkoxy, or with the group —NHC$_{1-6}$-alkyl or —N-di-C$_{1-6}$-alkyl, or together stand for a carbonyl group, or together form a cyclic five- or six-ring-acetal of the structure

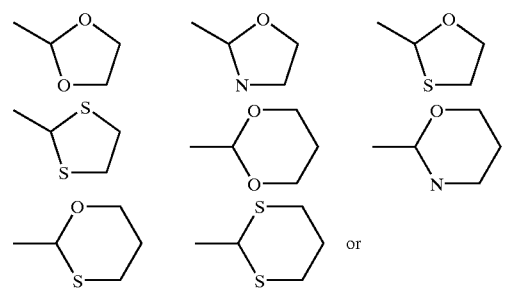

$R^2$ and $R^4$ together form a $C_3$–$C_{12}$-cycloalkyl ring or a $C_3$–$C_{12}$-cycloalkenyl ring, which optionally can be substituted with hydroxy, halogen, amino, $C_{1-6}$-alkoxy, or with the group —NHC$_{1-6}$-alkyl or —N-di-C$_{1-6}$-alkyl, or $R^3$ and $R^5$ together form a $C_3$–$C_{12}$-cycloalkyl ring or a $C_3$–$C_{12}$-cycloalkenyl ring, which optionally can be substituted with hydroxy, halogen, amino, $C_{1-6}$-alkoxy, or with the group —NHC$_{1-6}$-alkyl or —N-di-C$_{1-6}$-alkyl, $R^6$ and $R^7$ are the same or different and stand for hydrogen, linear or branched $C_1$–$C_6$-alkyl, $C_2$–$C_6$- alkenyl or $C_2$–$C_6$-alkinyl, which optionally can be substituted with hydroxy, halogen, amino, $C_{1-6}$-alkoxy, or with the group —$NHC_{1-6}$-alkyl or —N-di-$C_{1-6}$-alkyl, or together form a $C_3$–$C_{12}$-cycloalkyl ring or a $C_3$–$C_{12}$-cycloalkenyl ring, which optionally can be substituted with hydroxy, halogen, amino, $C_{1-6}$-alkoxy, or with the group —$NHC_{1-6}$-alkyl or —N-di-$C_{1-6}$-alkyl, or $R^5$ and $R^6$ optionally together form a double bond, T stands for —$CH_2$—, —O—, —$CH_2$=$CH_2$—, —CH≡CH—, —$CH_2$—O—$CH_2$—, —$CH_2$—O—, —O—$CH_2$— or =CO, and n stands for 0–6, or a tautomer, isomer or salt thereof.

3. A compounds of general formula I, according to claim 1, wherein $R^1$ stands for linear or branched $C_1$–$C_6$-alkyl, $C_2$–$C_6$-alkenyl, $C_2$–$C_6$-alkinyl, $C_1$–$C_6$-alkoxy, $C_1$–$C_6$-alkylthio or $C_3$–$C_{12}$-cycloalkyl, $C_3$–$C_{12}$-cycloalkenyl, $C_3$–$C_{12}$-heterocycloalkyl, $C_3$–$C_{12}$-heterocycloalkenyl, aryl or heteroaryl, which optionally can be substituted with hydroxy, halogen, amino, $C_{1-6}$-alkyl, $C_{1-6}$-alkoxy, $C_{1-6}$-alkylthio, halo-$C_{1-6}$-alkyl, halo-$C_{1-6}$-alkoxy, $C_{1-6}$-alkoxycarbonyl, cyano, nitro, $C_{1-6}$-alkylsulfanyl, $C_{1-6}$-alkylsulfinyl, $C_{1-6}$-alkylsulfonyl, or with the group —C(O)$C_{1-6}$-alkyl, —$NHC_{1-6}$-alkyl, —N-di-$C_{1-6}$-alkyl, —$CONH_2$, —$CONHC_{1-6}$-alkyl or —CON-di-$C_{1-6}$-alkyl, or can be substituted with another aryl or heteroaryl radical, which optionally itself can be substituted with hydroxy, halogen, amino, $C_{1-6}$-alkyl, $C_{1-6}$-alkoxy, $C_{1-6}$-alkylthio, halo-$C_{1-6}$-alkyl, halo-$C_{1-6}$-alkoxy, $C_{1-6}$-alkoxycarbonyl, cyano, nitro, $C_{1-6}$-alkylcarbonyl, $C_{1-6}$-alkylsulfanyl, $C_{1-6}$-alkylsulfinyl, $C_{1-6}$-alkylsulfonyl, or with the group —C(O)$C_{1-6}$-alkyl, —$NHC_{1-6}$-alkyl, —N-di-$C_{1-6}$-alkyl, —$CONH_2$, —$CONHC_{1-6}$-alkyl or —CON-di-$C_{1-6}$-alkyl, $R^2$ and $R^3$ are the same or different and stand for hydrogen, linear or branched $C_1$–$C_6$-alkyl, $C_2$–$C_6$-alkenyl, $C_2$–$C_6$-alkinyl or $C_1$–$C_6$-alkoxy, which optionally can be substituted with hydroxy, halogen, amino, $C_{1-6}$-alkoxy, or with the group —$NHC_{1-6}$-alkyl or —N-di-$C_{1-6}$-alkyl, $R^4$ and $R^5$ are the same or different and stand for hydrogen, halogen, linear or branched $C_1$–$C_6$-alkyl, $C_2$–$C_6$-alkenyl, $C_2$–$C_6$-alkinyl or $C_1$–$C_6$-alkoxy, which optionally can be substituted with hydroxy, halogen, amino, $C_{1-6}$-alkoxy, or with the group —$NHC_{1-6}$-alkyl or —N-di-$C_{1-6}$-alkyl, or together stand for a carbonyl group, or together form a cyclic five- or six-ring-acetal of the structure

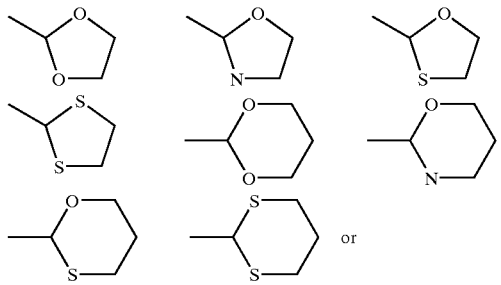

$R^2$ and $R^4$ together form a $C_3$–$C_{12}$-cycloalkyl ring or a $C_3$–$C_{12}$-cycloalkenyl ring, which optionally can be substituted with hydroxy, halogen, amino, $C_{1-6}$-alkoxy, or with the group —$NHC_{1-6}$-alkyl or —N-di-$C_{1-6}$-alkyl, or $R^3$ and $R^5$ together form a $C_3$–$C_{12}$-cycloalkyl ring or a $C_3$–$C_{12}$-cycloalkenyl ring, which optionally can be substituted with hydroxy, halogen, amino, $C_{1-6}$-alkoxy, or with the group —$NHC_{1-6}$-alkyl or —N-di-$C_{1-6}$-alkyl, $R^6$ and $R^7$ are the same or different and stand for hydrogen, linear or branched $C_1$–$C_6$-alkyl, $C_2$–$C_6$-alkenyl or $C_2$–$C_6$-alkinyl, which optionally can be substituted with hydroxy, halogen, amino, $C_{1-6}$-alkoxy, or with the group —$NHC_{1-6}$-alkyl or —N-di-$C_{1-6}$-alkyl, or together form a $C_3$–$C_{12}$-cycloalkyl ring or a $C_3$–$C_{12}$-cycloalkenyl ring, which optionally can be substituted with hydroxy, halogen, amino, $C_{1-6}$-alkoxy, or with the group —$NHC_{1-6}$-alkyl or —N-di-$C_{1-6}$-alkyl, or $R^5$ and $R^6$ optionally together form a double bond, T stands for —$CH_2$—, —O—, —$CH_2$=$CH_2$—, —CH≡CH—, —$CH_2$—O—$CH_2$—, —$CH_2$—O—, —O—$CH_2$— or =CO, and n stands for 0–6, or a tautomer, isomer or salt thereof.

4. A compounds of general formula I, according to claim 1, wherein $R^1$ stands for linear or branched $C_1$–$C_6$-alkyl, $C_2$–$C_6$-alkenyl, $C_2$–$C_6$-alkinyl, $C_1$–$C_6$-alkoxy, $C_1$–$C_6$-alkylthio or cyclopropyl, cyclobutyl, cyclopentyl, cyclohexyl, cycloheptyl, cyclooctyl, cyclononyl, cyclodecyl, norbornyl, adamantanyl, cyclobutenyl, cyclopentenyl, cyclohexenyl, cycloheptenyl, cyclooctenyl, cyclononenyl or cyclodecenyl, oxiranyl, oxethanyl, aziridinyl, azetidinyl, tetrahydrofuranyl, pyrrolidinyl, dioxolanyl, imidazolidinyl, pyrazolidinyl, dioxanyl, piperidinyl, morpholinyl, dithianyl, thiomorpholinyl, piperazinyl, trithianyl, quinuclidinyl, pyrrolinyl, imidazolinyl, pyrazolinyl, pyranyl, thiinyl, dihydroazetyl, cyclopropenyl, cyclopentadienyl, phenyl, tropyl, cyclooctadienyl, indenyl, naphthyl, biphenyl, azulenyl, fluorenyl, anthracenyl, thienyl, furanyl, pyrrolyl, oxazolyl, thiazolyl, imidazolyl, pyrazolyl, isoxazolyl, isothiazolyl, oxadiazolyl, triazolyl, thiadiazolyl, benzofuranyl, benzothienyl, pyridyl, pyridazinyl, pyrimidinyl, pyrazinyl, triazinyl, oxepinyl, azocinyl, indolizinyl, indolyl, isoindolyl, indazolyl, benzimidazolyl, purinyl, quinolinyl, isoquinolinyl, cinnolinyl, phthalazinyl, quinazolinyl, quinoxalinyl, naphthyridinyl, pteridinyl, carbazolyl, acridinyl, phenazinyl, phenothiazinyl, 1,3-benzodioxol-5-yl, phenoxazinyl or xanthenyl, which optionally can be substituted with hydroxy, halogen, amino, $C_{1-6}$-alkyl, $C_{1-6}$-alkoxy, $C_{1-6}$-alkylthio, halo-$C_{1-6}$-alkyl, halo-$C_{1-6}$-alkoxy, $C_{1-6}$-alkoxycarbonyl, cyano, nitro, $C_{1-6}$-alkylsulfanyl, $C_{1-6}$-alkylsulfinyl, $C_{1-6}$-alkylsulfonyl, or can be substituted with the group —C(O)$C_{1-6}$-alkyl, —$NHC_{1-6}$-alkyl, —N-di-$C_{1-6}$-alkyl, —$CONH_2$, —$CONHC_{1-6}$-alkyl or —CON-di-$C_{1-6}$-alkyl, or can be substituted with another aryl or heteroaryl radical, which optionally itself can be substituted with hydroxy, halogen, amino, $C_{1-6}$-alkyl, $C_{1-6}$-alkoxy, $C_{1-6}$-alkylthio, halo-$C_{1-6}$-alkyl, halo-$C_{1-6}$-alkoxy, $C_{1-6}$-alkoxycarbonyl, cyano, nitro, $C_{1-6}$-alkylcarbonyl, $C_{1-6}$-alkylsulfanyl, $C_{1-6}$-alkylsulfinyl, $C_{1-6}$-alkylsulfonyl, or with the group —C(O)$C_{1-6}$-alkyl, —$NHC_{1-6}$-alkyl, —N-di-$C_{1-6}$-alkyl, —$CONH_2$, —$CONHC_{1-6}$-alkyl or —CON-di-$C_{1-6}$-alkyl, $R^2$ and $R^3$ are the same or different and stand for hydrogen, linear or branched $C_1$–$C_6$-alkyl, $C_2$–$C_6$-alkenyl, $C_2$–$C_6$-alkinyl or $C_1$–$C_6$-alkoxy, which optionally can be substituted with hydroxy, halogen, amino, $C_{1-6}$-alkoxy, or with the group —$NHC_{1-6}$-alkyl or —$N$-di-$C_{1-6}$-alkyl, $R^4$ and $R^5$ are the same or different and stand for hydrogen, halogen, linear or branched $C_1-C_6$-alkyl, $C_2-C_6$-alkenyl, $C_2-C_6$-alkinyl or $C_1-C_6$-alkoxy, which optionally can be substituted with hydroxy, halogen, amino, $C_{1-6}$-alkoxy, or with the group —$NHC_{1-6}$-alkyl or —$N$-di-$C_{1-6}$-alkyl, or together stand for a carbonyl group, or together form a cyclic five- or six-ring-acetal of the structure

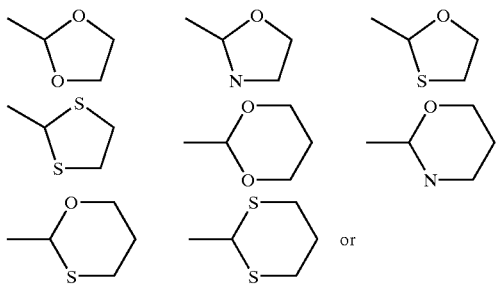

$R^2$ and $R^4$ together form a $C_3-C_7$-cycloalkyl ring or a $C_3-C_7$-cycloalkenyl ring, which optionally can be substituted in one or more places in the same way or differently with hydroxy, halogen, amino, $C_{1-6}$-alkoxy, or with the group —$NHC_{1-6}$-alkyl or —$N$-di-$C_{1-6}$-alkyl, or $R^3$ and $R^5$ together form a $C_3-C_7$-cycloalkyl ring or a $C_3-C_7$-cycloalkenyl ring, which optionally can be substituted with hydroxy, halogen, amino, $C_{1-6}$-alkoxy, or with the group —$NHC_{1-6}$-alkyl or —$N$-di-$C_{1-6}$-alkyl, $R^6$ and $R^7$ are the same or different and stand for hydrogen, linear or branched $C_1-C_6$-alkyl, $C_2-C_6$-alkenyl or $C_2-C_6$-alkinyl, which optionally can be substituted with hydroxy, halogen, amino, $C_{1-6}$-alkoxy, or with the group —$NHC_{1-6}$-alkyl or —$N$-di-$C_{1-6}$-alkyl, or together form a $C_3-C_7$-cycloalkyl ring or a $C_3-C_7$-cycloalkenyl ring, which optionally can be substituted with hydroxy, halogen, amino, $C_{1-6}$-alkoxy, or with the group —$NHC_{1-6}$-alkyl or —$N$-di-$C_{1-6}$-alkyl, or $R^5$ and $R^6$ optionally together form a double bond, T stands for —$CH_2$—, —O—, —$CH_2$=$CH_2$—, —CH≡CH—, —$CH_2$—O—$CH_2$—, —$CH_2$—O—, —O—$CH_2$— or =CO, and n stands for 0–6, or a tautomer, isomer or salt thereof.

5. A compounds of general formula I, according to claim 1, wherein $R^1$ stands for $C_1-C_6$-alkylthio, phenyl, biphenyl, thienyl, cyclopropyl, cyclohexyl, pyridyl, naphthyl, 1,3-benzodioxol-5-yl or isoxazolyl, which optionally can be substituted with halogen, amino, cyano, $C_{1-6}$-alkylsulfonyl, $C_{1-6}$-alkyl, halo-$C_{1-6}$-alkyl, $C_{1-6}$-alkoxy, $C_{1-6}$-alkylthio, or with the group —C(O)$C_{1-6}$-alkyl, or which can be substituted with phenyl, thienyl, naphthyl, pyridyl, furanyl or pyrimidinyl, which optionally itself can be substituted with $C_{1-6}$-alkyl, $C_{1-6}$-alkoxy, amino, $C_{1-6}$-alkylsulfonyl, cyano or with the group —C(O)$NH_2$, $R^2$, $R^3$, $R^4$, $R^5$, $R^6$ and $R^7$ stand for hydrogen or $C_{1-6}$-alkyl, T stands for the group —$CH_2$—, —$CH_2$—O—$CH_2$— or —$CH_2$—O—, and n stands for 0–2, or a tautomer, isomer or salt thereof.

6. Compounds of general formula II

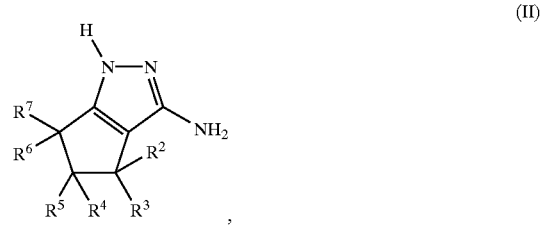

(II)

in which $R^2$, $R^3$, $R^4$, $R^5$, $R^6$ and $R^7$ have the meanings that are indicated in general formula I, according to claim 1.

7. A method of treating: leukemia; psoriasis; mucositis; alopecia; multiple sclerosis; stenoses; arterioscleroses; restenoses; a unicellular parasitic disease; glomerulonephritis; Huntington's disease; amylotrophic lateral sclerosis; Parkinson's disease; AIDS dementia; Alzheimer's disease; an ischemia of the brain; neurotrauma; a cytomegalic infection; herpes; Hepatitis B or C; or HIV infection, which comprises administering an effective amount of a compound of claim 1 to a patient.

8. A pharmaceutical composition comprising a compound according to claim 1 and at least one suitable carrier or vehicle.

9. A pharmaceutical composition of claim 8, which is in a form for enteral, parenteral or oral administration.

* * * * *